(12) United States Patent
Stoecker

(10) Patent No.: US 10,874,555 B2
(45) Date of Patent: Dec. 29, 2020

(54) WOUND DRESSING

(71) Applicant: Stoecker & Associates LLC, Rolla, MO (US)

(72) Inventor: William Van Dover Stoecker, Rolla, MO (US)

(73) Assignee: Stoecker & Associates LLC, Rolla, MO (US)

( * ) Notice: Subject to any disclaimer, the term of this patent is extended or adjusted under 35 U.S.C. 154(b) by 469 days.

(21) Appl. No.: 15/694,216

(22) Filed: Sep. 1, 2017

(65) Prior Publication Data

US 2018/0064841 A1 Mar. 8, 2018

Related U.S. Application Data

(60) Provisional application No. 62/383,172, filed on Sep. 2, 2016.

(51) Int. Cl.
| | |
|---|---|
| *A61L 15/18* | (2006.01) |
| *A61F 13/02* | (2006.01) |
| *A61F 13/00* | (2006.01) |
| *A61L 15/44* | (2006.01) |
| *A61F 17/00* | (2006.01) |

(52) U.S. Cl.
CPC .... *A61F 13/00063* (2013.01); *A61F 13/0216* (2013.01); *A61F 17/00* (2013.01); *A61L 15/18* (2013.01); *A61L 15/44* (2013.01); *A61L 2300/102* (2013.01)

(58) Field of Classification Search
CPC ..... A61L 15/18; A61K 2121/00; A61F 13/00; A61F 13/00063–0008; A61F 13/02–0226
See application file for complete search history.

(56) References Cited

U.S. PATENT DOCUMENTS

| | | | | | |
|---|---|---|---|---|---|
| 2,432,541 | A | * | 12/1947 | McClelland | A61F 13/0203 602/48 |
| 2,579,403 | A | * | 12/1951 | Slomowitz | A61F 13/0203 604/306 |
| 5,556,375 | A | * | 9/1996 | Ewall | A61F 13/0203 602/43 |
| 5,607,388 | A | * | 3/1997 | Ewall | A61F 13/023 602/46 |
| 5,976,117 | A | * | 11/1999 | Dunshee | A61F 13/0203 602/41 |

(Continued)

*Primary Examiner* — Susan S Su
(74) *Attorney, Agent, or Firm* — Faegre Drinker Biddle & Reath LLP

(57) ABSTRACT

Embodiments disclosed herein provide compositions, methods, and uses for treating skin wounds, including chronic wounds such as venous ulcers. Certain embodiments provide methods for treating a skin wound, where the entire wound is exposed to zinc, especially in the form of zinc gauze. Certain embodiments provide methods for treating a skin wound, where only a peripheral rim of the wound is exposed to zinc, especially in the form of zinc oxide gauze. Other embodiments provide wound dressings and wound dressing kits, where the dressing and dressing kits include central gauze free of zinc to contact a central drainage zone of the wound and a second zinc gauze to contact a peripheral healing zone of the wound. In certain embodiments, the central gauze is optional.

17 Claims, 20 Drawing Sheets

(56) References Cited

U.S. PATENT DOCUMENTS

| | | | |
|---|---|---|---|
| 7,070,584 B2* | 7/2006 | Johnson | A61M 1/0088 424/444 |
| 7,569,742 B2* | 8/2009 | Haggstrom | A61F 13/0203 602/53 |
| 2010/0274205 A1* | 10/2010 | Morelli | A61M 1/0088 604/290 |
| 2015/0209186 A1* | 7/2015 | Abbott | A61L 15/18 602/48 |
| 2016/0022505 A1* | 1/2016 | Igwebuike | A61F 13/00063 602/42 |
| 2016/0220606 A1* | 8/2016 | Matouk | A61F 13/00063 |

* cited by examiner

WOUND DRESSING

FIELD

This disclosure relates to compositions, methods, and uses for treating skin wounds, including chronic wounds and non-healing wounds.

BACKGROUND

Non-healing wounds place tremendous burdens on medical systems. These wounds include surgical wounds, traumatic wounds, necrotic wounds due to pharmaceutical agents or biological envenomations, (the preceding wounds collectively termed secondary intention wounds), diabetic ulcers, and one important source of chronic wounds: venous ulcers. Venous ulcers alone account for 1.3-2% of total medical expenses in developed countries. It is estimated that 500,000-2 million people in the United States develop venous leg ulcers every year, with the prevalence expected to increase as the population ages and as the prevalence of obesity and diabetes mellitus increases. Three types of non-healing wounds comprise the great majority of these non-healing wounds, and include 1) venous leg ulcers, 2) diabetic ulcers, and 3) pressure ulcers. A fourth type of wound called a secondary intention wound generally occurs in persons without compromised healing.

Venous leg ulcers (VLU), caused by chronic venous insufficiency, comprise an estimated 50% to 70% of leg ulcers, with a prevalence of 1% to 1.5%. Patient history can include deep venous thrombosis, trauma, or surgery to the lower leg. VLUs most often appear in the "gaiter region," which extends from mid-calf to approximately 2.5 cm below the malleolus.

Venous ulcers are typically slow to heal, with many patients suffering from open wounds for months at a time. For venous leg ulcers present for at least six weeks, it is estimated that over 50% of the ulcers are not healed after one year. Even after complete healing, there is an estimated 72% overall recurrence rate, with a 21% chance that the ulcer will recur within one year. The combination of slow healing, high recurrence rates and the high level of care required to apply treatments of moderate complexity often results in multiple clinic visits for each ulcer, heavily impacting annual healthcare costs. A large portion of these costs is attributable to long-term treatments, such as Unna boot therapy and standard compression therapy, both of which require frequent dressing changes by someone with training in ulcer care and dressing application.

The Unna boot, a compression dressing, is a standard mode of treatment for venous ulcers. Unna boot therapy utilizes a gauze compression wrap (the Unna boot, or Unna boot dressing impregnated with a paste of zinc oxide, demonstrated to be beneficial in the healing of ulcers. However, the rate of healing with Unna boots is slow, in the range of 4-5% per week. Studies have shown that fewer than half of these ulcers heal after a course of six weeks or more of Unna boot therapy. As a result, patients may become noncompliant, further lengthening the duration of time required for full healing. Wound dressings for other chronic wounds and those conditions resembling chronic wounds, face similar limitations—slow healing and a requirement for professional medical care.

Diabetic foot ulcers are present in an estimated 2%-4% of patients with diabetes, and are the leading cause of amputation. The estimated lifetime risk of developing a diabetic foot ulcer may be as high as 25%. Infection is common in diabetic foot ulcers. Poor glucose control leads to reduced microcirculation, while damage to nerves (diabetic neuropathy) can lead to repetitive trauma on certain areas of the feet, particularly on the plantar surface. These ulcers are very slow to heal; requiring a multidisciplinary team to implement local wound management, control of diabetes, and prevention of infection. Those who do not adhere well to treatment may obtain a chronic ulcer and/or may worsen to the point of amputation. For those ulcers that do heal, the average time to heal for a diabetic foot ulcer, is 70-133 days. The median diabetic foot ulcer size is approximately 1×1.5 cm (radius approximately 1.25 cm), with a median healing time of approximately 100 days. Using these estimates, healing rates for diabetic foot ulcers are 0.045 $mm^2$/day. Average radius reduction has been cited as 0.5 mm/week. For an approximately circular ulcer, this is equivalent to an area reduction of 0.11 $mm^2$/day. Another study showed a range of reduction of 0.0065-0.045 mm/day radius reduction, which for an approximately circular ulcer is equivalent to an area reduction (healing rate) of 0001 to 0.006 $mm^2$/day. The range of healing rate for diabetic foot ulcers is large and the healing rate is entirely dependent on a multidisciplinary team and patient compliance. Recurrence is the norm for diabetic foot ulcers. Treatment generally includes glucose control, exercise, avoidance of long periods of standing, diabetic shoes, and other methods of offloading, infection control, and other wound care measures including debridement. Convincing evidence supporting one dressing over another is not available. The main issues with current treatment are the extremely slow healing rates, high incidence of infection, and high incidence of failure to heal and complications such as osteomyelitis and infection.

Another class of wounds is pressure ulcers (PU), often previously called decubitus ulcers. A change in Medicare payment policies reduced the reported incidence of pressure ulcers in hospitals over 90%, yet pressure ulcers still cost the healthcare system over $11 billion. The sites most commonly affected by PU are the sacrum (28%), heels, (23.6%), and buttocks, including both posterior (ischial tuberosity) and lateral (greater trochanter) area (17.2%). Overall pressure ulcer prevalence rates in a survey including acute care, long-term acute care, and long-term care facilities (99% of facilities in the US) were approximately 10%, with the highest prevalence documented in long-term acute care facilities (27.3%). Recurrence of these ulcers is frequent. Failure to heal may lead to inpatient surgery, with more complex surgery with, for example, myocutaneous flaps, which are favored over simple skin grafting because of the protection offered by the muscle layer. As in the case of other ulcers, evidence regarding superiority of one type of dressing over another is minimal Management goals for these ulcers center around relief of pressure at the points prone to ulceration. Treatment strategies cover pressure-relieving equipment, adjusting mattress type, mobility aids, and nutrition.

Secondary intention wounds are wounds that are left open to heal. This class of wounds may generally be described as those resulting from any traumatic or surgical injury. With surgical injury, therapy may be the choice of physician or patient. Such wounds can take 3-4 weeks to heal, but can take longer, over two months, even in patients without adverse factors for healing. Wounds healed by secondary intention in the end may have very acceptable cosmetic outcome. The healing rate of secondary intention wounds after skin cancer surgery has been shown to be approximately 14 $mm^2$/day with bioengineered skin, in one small study.

SUMMARY

Embodiments disclosed herein provide compositions, methods, and uses for treating skin wounds, including chronic wounds such as venous ulcers, secondary intention wounds, and diabetic ulcers. Certain embodiments provide methods for treating a skin wound, where only a peripheral rim of the wound is exposed to zinc. Other embodiments provide wound dressings and wound dressing kits, where the dressing kits include either zinc gauze or central gauze free of zinc to contact a central drainage zone of the wound, and zinc gauze to contact a peripheral healing zone of the wound. Some embodiments provide wound dressings and wound dressing kits for dressing wounds wherein dressings and dressing kits include zinc gauze and an adhesive layer. Some embodiments of wound dressings and wound dressing kits do not have a central gauze, and such embodiments can be used for a variety of wound sizes.

In certain embodiments, the provided methods and compositions can be applied to, for example, chronic wounds, those conditions resembling chronic wounds, and other secondary intention wounds where wound healing is not compromised. In certain embodiments, methods and compositions of the present disclosure can be used to dress, for example, venous leg ulcers, diabetic ulcers, pressure ulcers, cancer-related lesions, dermonecrosis lesions, and other wounds.

Certain embodiments described in the present disclosure provide wound dressings including a central drainage gauze configured to occupy an approximately central area in a wound such that from about 2 mm to about 10 mm of the wound periphery is not covered by the central drainage gauze and a zinc gauze configured to occupy the exposed wound periphery not covered by the central drainage gauze.

Other embodiments described in the present disclosure provide wound dressing kits including a central drainage gauze configured to occupy an approximately central area in a wound such that from about 2 mm to about 10 mm of the wound periphery is not covered by the central drainage gauze and a zinc gauze configured to occupy the exposed wound periphery not covered by the central drainage gauze. In some embodiments, the kits can also include a physiological solution. In some embodiments, the kits can include a retention layer. In certain embodiments, the zinc gauze is affixed to an adhesive strip.

Yet other embodiments described in the present disclosure provide methods to dress a wound, where the method includes cutting or manufacturing a central drainage gauze, wherein the cut central drainage gauze leaves an exposed periphery of the wound having a width of about 2 mm to about 10 mm when placed approximately centrally in the wound, placing the cut central drainage gauze approximately centrally in the wound, placing a zinc gauze over the wound and contacting the zinc gauze with the exposed periphery of the wound, and securing the dressing in place. In some embodiments, the central drainage gauze can be saturated with a physiological solution. In certain embodiments, the central drainage gauze can be saturated either before or after being placed approximately centrally in the wound.

Other embodiments described in the present disclosure provide a wound dressing including a zinc gauze configured to occupy an entirety of an exposed wound, and a retention layer configured to retain the zinc gauze on the exposed wound. In some embodiments, the exposed wound is a smaller wound. In some embodiments, the exposed wound is a larger wound with a minimal drainage. In some embodiments, the retention layer can be a section of adhesive strip in the shape of, for example, a rectangle, a square, or an oval.

BRIEF DESCRIPTION OF THE DRAWINGS

The following drawings form part of the instant specification and are included to further demonstrate certain aspects of particular embodiments herein. The embodiments may be better understood by reference to one or more of these drawings in combination with the detailed description presented herein.

DETAILED DESCRIPTION

Embodiments disclosed herein provide compositions, methods, and uses for treating skin wounds, including acute wounds and chronic wounds such as venous ulcers. Certain embodiments provide methods for treating a skin wound, where only a peripheral rim of the wound is exposed to zinc. Other embodiments provide wound dressings and wound dressing kits, where the dressings and dressing kits include central gauze free of zinc to contact a central drainage zone of the wound and a second zinc gauze to contact a peripheral healing zone of the wound. Yet other embodiments provide wound dressings and wound dressing kits for dressing a smaller wound, where the dressings and dressing kits include zinc gauze and an adhesive layer, which can be the composition for any size wound.

As used herein, the term "zinc gauze" includes gauze that has been impregnated with zinc, zinc oxide, zinc sulfate, zinc pyrithione, or zinc gluconate or had zinc, zinc oxide, zinc sulfate, zinc pyrithione, or zinc gluconate applied to the surface of the gauze.

Figure 1A:
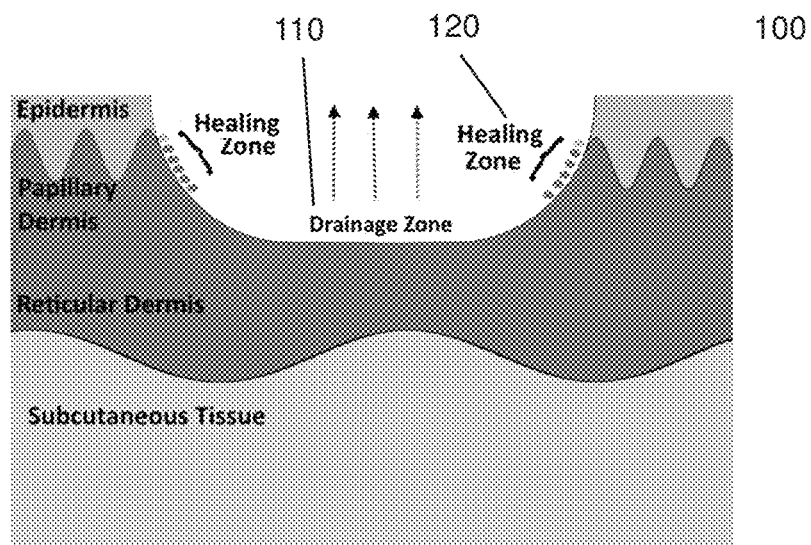
FIG. 1A is a schematic diagram representing the two-zoned structured wound healing model according to one embodiment of the present disclosure.
Figure 1B:
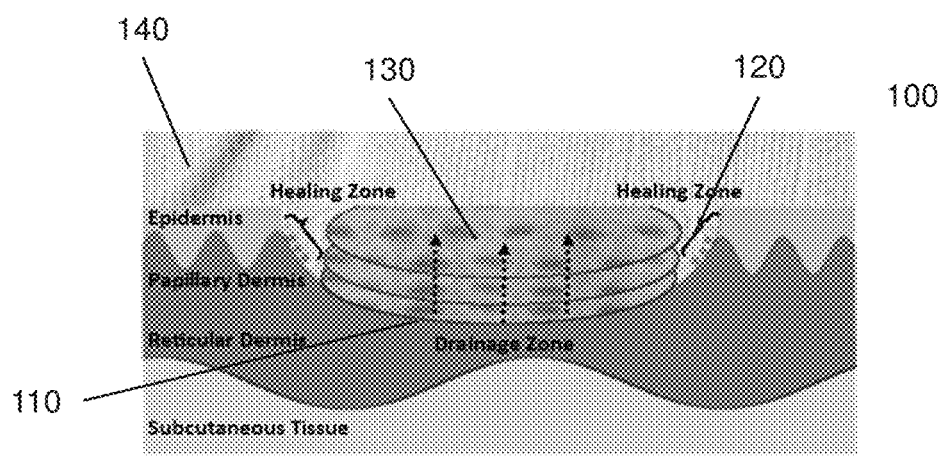
FIG. 1B is a schematic diagram representing the zinc rim protocol according to one embodiment of the present disclosure.

In certain aspects, methods for dressing wounds are provided. In certain cases, the provided methods for dressing wounds can be applied to, for example, chronic wounds, those conditions resembling chronic wounds, and other secondary intention wounds or other acute wounds where wound healing is not compromised. In certain embodiments, methods of the present disclosure can be used to dress, for example, venous leg ulcers, diabetic ulcers, pressure ulcers, cancer-related lesions such as open wounds after cancer treatments, dermonecrotic lesions as from arachnids or other arthropods, and other wounds. The methods are founded on a structured zone model for wound healing, as described in the present disclosure and represented in FIG. 1A. As depicted by FIG. 1A, the wound of the structured zone model for wound healing 100 includes a central drainage zone 110 and a peripheral healing zone 120. As illustrated by FIG. 1B, the methods of the present disclosure include placing a central drainage gauze 130 in the central drainage zone 110 and providing a zinc gauze 140 at the peripheral healing zone 120. In accordance with these methods, the central drainage gauze 130 is in direct contact with the central drainage zone 110 and the zinc gauze 140 is in direct contact with the peripheral healing zone 120. In certain embodiments, the zinc gauze 140 is laid over top of the central drainage gauze 120. In other embodiments, the central gauze is omitted entirely. Such an arrangement with the central gauze results in a two-tiered dressing where the zinc gauze 140 extends beyond the central drainage gauze 120 and contacts the peripheral healing zone, as illustrated in FIG. 1B.

In certain embodiments, a single piece of gauze can have more than one zone, wherein at least one of the zones contains zinc and at least one of the zones is zinc-free. In accordance with such embodiments, the zinc-free zone can be the central drainage zone and the zinc-containing zone can be a peripheral healing zone. The zinc gauze can be used alone or in combination with a second piece of gauze, such as the central drainage gauze 120. In such embodiments, the central drainage gauze 120 can be in direct contact with the central drainage zone 110, or can be configured to push the multi-zoned gauze downward and into contact with the central drainage zone 110.

The central drainage zone 110 and peripheral healing zone 120 have different physiological characteristics in terms of, for example, moisture, inflammation, and biofilm formation; this phenomenon forms the basis for the two-zoned structured model for wound healing 100. Soon after wound initiation, the central drainage zone displays characteristics of a chronic wound. In chronic non-healing wounds, upregulation of proinflammatory cytokines IL-1, IL-6 and tumor necrosis factor (TNFα) is prolonged, leading to impaired fibroblast activity and elevated metalloproteinases that degrade the local extracellular matrix, impair cell migration and delay healing. The crosstalk between the proinflammatory extracellular fluid and the cellular matrix can lead to delayed angiogenesis and myofibroblast differentiation, thereby slowing wound contraction. Wound healing can be further slowed by biofilm formation in the static wound center.

Fluid removal from the drainage zone reverses these processes and reduces compression of the microvasculature, favoring healing. If central drainage spills over into the healing zone, the pro-inflammatory cytokines will degrade the favorable peripheral cytokine balance and could spread the central biofilm. Removing excess central drainage is therefore critical for healing, particularly if such drainage is observed. Sponges designed for rapid wound drainage have been described as a connected 3-dimensional polyhedral lattice. The central gauze lattice (FIG. 9) promotes drainage in this manner.

A healthy peripheral healing zone 120 exhibits fast regeneration of epidermis and has a favorable inflammatory cytokine balance. The mobile wound margin is unlikely to develop a biofilm, and drainage is minimal. Activation of growth factors with zinc can promote fast healing in the peripheral healing zone 120. Local divalent zinc can speed up wound healing via activation of zinc-finger proteins (transcription factors that bind to DNA), which in turn promote angiogenesis.

Topical zinc has been shown to be superior to oral zinc supplementation in wound healing. Zinc plays a role in multiple phases including mitosis, migration, and maturation. Alkaline phosphatase (a zinc metalloenzyme), angiogenesis, and integrins including α2, α3, αv, and α6 integrin subunits are all upregulated in wound healing and are all dependent upon adequate local zinc levels. Zinc oxide, supplying divalent zinc needed as a co-factor for zinc metalloenzymes, is so beneficial for wound healing that in one study, supplied with iron, it was associated with faster healing than the comparison treatment of platelet-derived growth factor. Topical zinc can be applied to zinc-free gauze. However, applying topical zinc or a topical zinc dressing to the entire wound surface can diminish the potential healing advantage of zinc, as demonstrated by the common Unna dressing.

Zinc-containing dressings such as, for example, Unna boot dressings, are widely used in the treatment of chronic wounds, including ulcers (e.g., venous leg ulcers). However, healing rates observed in connection with current dressings such as the Unna boot are slow, in the range of 4-5% per week. Fewer than half of Unna boot dressing-treated ulcers heal after a course of six weeks or more. As a result, patients may become noncompliant, further lengthening the duration of time required for full healing.

Materials and methods of the present disclosure result in drainage (exudate) from the central drainage zone 110 being absorbed, thereby preventing spillover of drainage into the peripheral healing zone 120, where the drainage can degrade the favorable physiology of the peripheral drainage zone and spread the central biofilm. Absorbing the central drainage while leaving only the peripheral healing zone 120 in contact with the zinc gauze 140 allows the zinc to effectively promote healing at the wound periphery, particularly in larger wounds. With a common Unna dressing, the potential healing advantage of zinc may be diminished because of excess moisture.

In certain embodiments, the materials and methods of the present disclosure remove fluid from the central drainage zone 110, minimizing moisture at the peripheral healing zone 120 and reducing compression of the microvasculature, favoring healing. In some embodiments, the central drainage gauze 130 can be saturated with a physiological solution. In certain embodiments, the central drainage gauze can be saturated with physiological solution after being placed in the central drainage zone 110. In other embodiments, the central drainage gauze 130 can be saturated with physiological solution prior to being placed in the central drainage zone 110. Where the central drainage gauze 130 is saturated after being placed in the central drainage zone 110, care is taken not to oversaturate the wound. Soaking the central drainage gauze 130 with a physiological solution can help maintain healthy wound physiology by diluting the proinflammatory exudate, and aid in the wicking of exudate, among other mechanisms. The physiological solution can be any physiological solution known in the art. In some embodiments, the physiological solution is a saline solution. In particular embodiments, the physiological solution is a 0.9% saline solution.

According to the methods of some embodiments, the central drainage gauze 130 is cut to a size or provided in a size that when place in the central drainage zone 110, a zone of about 2 mm to about 10 mm is left at the wound periphery. The periphery can include all or a significant proportion of the peripheral healing zone. In some embodiments, the central drainage gauze 130 is of a size that results in a periphery of about 2 mm to about 4 mm. In a particular embodiment, the periphery is about 2 mm to about 3 mm. In other embodiments, the central drainage gauze 130 is of a size that results in a periphery of about 4 mm to about 6 mm. In a particular embodiment, the periphery is about 6 mm to about 8 mm. In yet another embodiment, the periphery is about 3 mm to about 5 mm. In certain embodiments, the size of the central drainage gauze is adjusted upon changing the dressing to account for changes in wound size. In some embodiments, particularly when a wound has more than one central drainage zone 110 or an irregularly shaped central drainage zone 110, more than one section of central drainage gauze 130 can be used in combination with one or more sections of zinc gauze 140 (see, e.g., FIG. 21). Such an arrangement can provide for a more uniform periphery to be formed relative to an arrangement having a single section of drainage gauze 130.

In some embodiments, the width of the periphery is adjusted dependent on the volume of drainage fluid produced by the wound. Where a wound produces a large amount of exudate, the size of the central drainage gauze 130 can be increased, leaving a narrower peripheral healing zone 120. Wounds producing a small to moderate amount of exudate can be treated using a smaller central drainage gauze 130, leaving a wider peripheral healing zone 120.

In certain embodiments, an extra layer of dry, absorbent gauze is placed over the wound (see, e.g., FIGS. 8 and 15-18). The extra layer of dry, absorbent gauze can aid in absorption of excess exudate. This can help increase the interval between dressing changes, and can help improve the effectiveness of the dressing method by maintaining physiological conditions at the central drainage zone 110 that are conducive to healing and prevent saturation and the resulting impairment of healing of the peripheral healing zone 120. In some embodiments, the extra layer of dry, absorbent gauze is of similar size and shape as the central drainage gauze 130. In certain embodiments, the extra layer of dry, absorbent gauze can be placed directly on top of physiological solution-soaked central drainage gauze 130. The zinc gauze 140 can then be placed overtop the stack of extra layer of dry, absorbent gauze and the physiological solution-soaked central drainage gauze 130. In such an arrangement, the zinc gauze 140 is not impeded from coming into contact with the peripheral healing zone 120. In other embodiments, the extra layer of dry, absorbent gauze can be placed on the zinc gauze 140, where the zinc gauze 140 has been placed over the central drainage gauze 130. In such an arrangement, the extra layer of dry, absorbent gauze can be larger than the central drainage gauze 130.

In certain embodiments, the zinc gauze 140 is a wrap-type dressing or compression dressing. In some embodiments, the zinc gauze 140 is a Unna boot dressing. In some embodiments, the zinc gauze 140 is regular gauze to which a layer of topical zinc or zinc oxide has been applied. In certain embodiments, the method for treating a wound includes placing the central drainage gauze 130 in the wound at the central drainage zone 110 and wrapping the wound with the zinc gauze 140. In such an embodiment, the size of the central drainage gauze 130 is selected to leave a peripheral healing zone 120 having a desired width. Upon wrapping the wound with the central drainage gauze 130 in place, the peripheral healing zone 120 is brought into contact with the zinc gauze 140. In some embodiments, there is a membrane between the zinc gauze 140 and the central drainage gauze 130. Such a membrane may be permeable, semi-permeable, or non-permeable. In general, any size and shape of dressing may be considered, with the most useful shapes, whether oval or rectangular, somewhat longer than wide.

Figure 2:
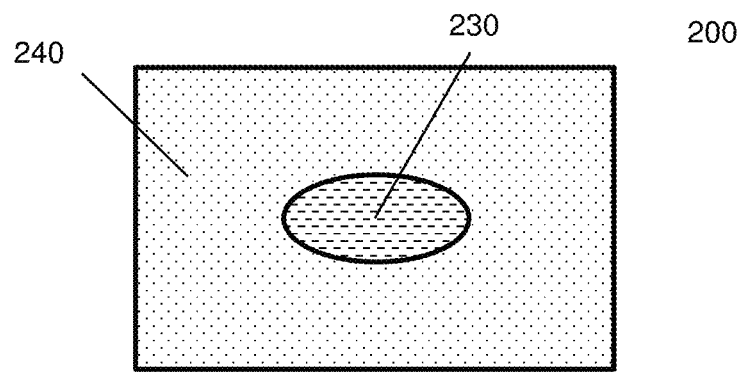
FIG. 2 is a schematic diagram representing a wound dressing according to one embodiment of the present disclosure.

In other embodiments, the zinc gauze 140 is provided in a size that extends beyond the borders of the wound, but is not in the form of a wrap or compression dressing (see, e.g., FIG. 2). In such embodiments, the zinc gauze 140 can be held in place over the wound by an adhesive strip or a wrap. Referring now to FIG. 3, in certain embodiments, the zinc gauze 340 is held in place by retention layer 350. In other embodiments, the zinc gauze 140 is held in place by a wrap, such as, for example, a compression bandage. In some embodiments, the wound may be further treated with topical medical grade Manuka honey or systemic horse chestnut seed extract.

Figure 16:
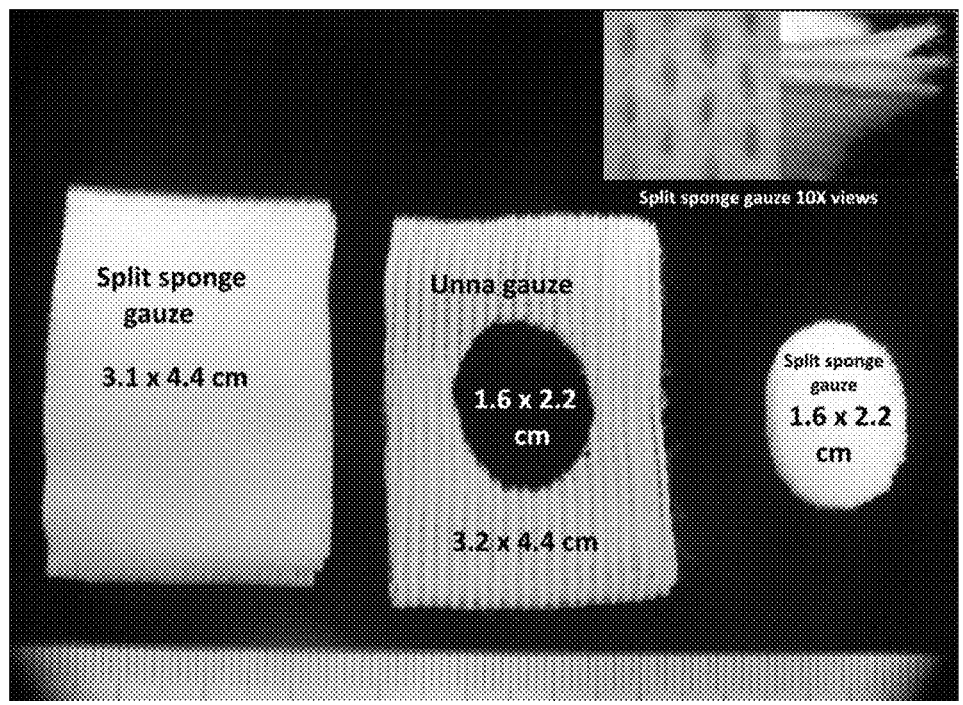
FIG. 16 is a photograph of examples of gauze used in a wound dressing according to one embodiment of the present disclosure.

In other embodiments, the zinc gauze 140 has an approximately centrally located cutout, or fenestration (see, e.g., FIG. 16). Central drainage gauze 130 can be placed in the cutout, allowing the central drainage gauze 130 and zinc gauze 140 to lay approximately flush with the wound. This arrangement can ensure that zinc gauze 140 remains in effective contact with the peripheral healing zone 120, particularly when extra layers of dry gauze are required to absorb excess drainage. In certain embodiments, central drainage gauze 130 can be placed in a cutout of zinc gauze 140, and because of this arrangement, the central drainage gauze 130 can be in direct contact with the extra layers of dry gauze. In certain embodiments the central drainage gauze 130 and extra layers of dry gauze are a single unit, with a portion of the gauze being forced through the cutout in zinc gauze. In such an arrangement, the size of the central drainage gauze 130 can be controlled by the size of the cutout in zinc gauze 140. In some embodiments, the cutout in the zinc gauze is large enough to only let a small portion, or 'wick', of the central drainage gauze 130 to extend through the zinc gauze 140. In other embodiments, the wick is a different absorbent material that is not the central drainage gauze 130 (e.g., PolyMem® absorbent dressing). Is such embodiments including a wick, the wick can function to pass drainage from the wound absorbed by the central drainage gauze 130 to extra layers of dry gauze.

Referring to FIG. 2, the method for treating a wound using a wound dressing 200 of some embodiments includes placing the central drainage gauze 230 in a wound to be treated, leaving a peripheral healing zone having a desired width exposed. The zinc gauze 240 is then place over the central drainage gauze 230 and brought into contact with the peripheral healing zone. The dressed wound is then wrapped with, for example, with a compression bandage, which serves to keep the dressing in place (see, e.g., FIG. 8).

Figure 3A:
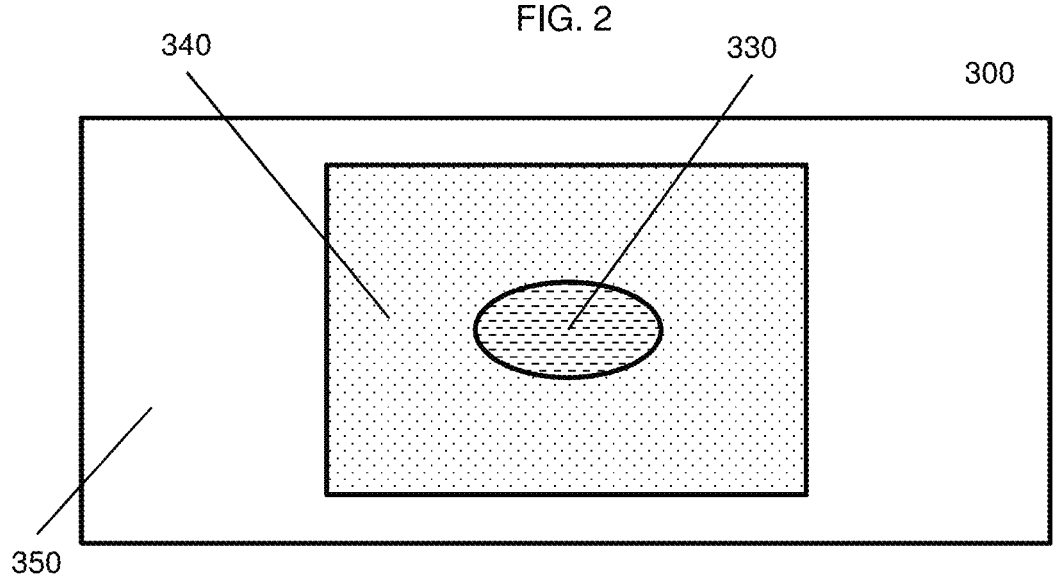
FIGS. 3A-3B are schematic diagrams representing wound dressings according to embodiments of the present disclosure.

Referring to FIG. 3A, the method for treating a wound using a wound dressing 300 of another embodiment includes placing the central drainage gauze 330 in a wound to be treated leaving a peripheral healing zone having a desired width exposed. The zinc gauze 340 is then placed over the central drainage gauze 330 and brought into contact with the peripheral healing zone. A retention layer 350 is then placed over the dressed wound to keep the dressing in place. In another embodiment, the zinc gauze 340 is affixed to the retention layer 350 prior to application to the wound (see, e.g., FIG. 23B), and the resulting adhesive strip with attached zinc gauze is place over the wound dressed with the central drainage gauze 330 (see, e.g., FIG. 7).

Figure 3B:
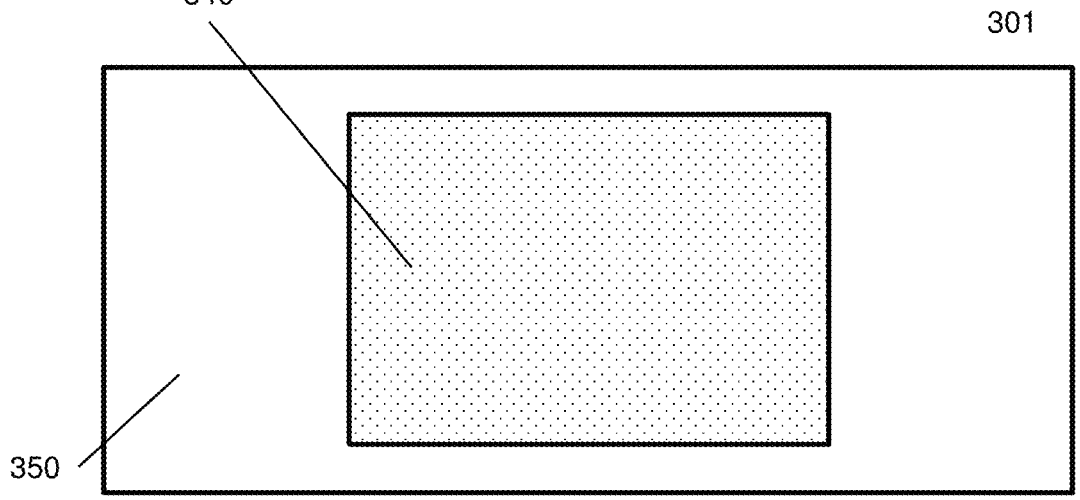

In another embodiment, referring to FIG. 3B, the method for treating a wound using a wound dressing 301 includes placing zinc gauze 340 over the wound. A retention layer 350 is then placed over the dressed wound to keep the dressing in place. In another embodiment, the zinc gauze 340 is affixed to the retention layer 350 prior to application to the wound (see, e.g., FIG. 23A), and the resulting adhesive strip with attached zinc gauze is place over the wound dressed.

In some embodiments, the retention layer can be an adhesive strip. Any adhesive material capable of holding the central drainage gauze/zinc gauze dressing in place can be used. The material selected for the adhesive strip can depend on the desired application. For example, the adhesive strip can be breathable and/or water resistant, and can be latex-free.

In certain embodiments, methods for treating a wound using the zinc rim protocol described herein also include preparation of the wound prior to dressing. Venous ulcers, for example, frequently require debridement of necrotic tissue prior to dressing the wound. Wounds to be treated by the zinc rim protocol described herein can be prepared by any means known in the art, including debridement. Debridement can be carried out by, for example, wet-to-dry saline soaks or physical debridement. Following preparation of the wound, the wound can be dressed by the methods described in the present disclosure. The method described may eliminate the need for debridement, as zinc oxide has been shown to provide debridement.

In other embodiments, the central drainage gauze 130 can be omitted. This is possible in the instance of smaller wounds, particularly those having an area of less than about 1.6 cm². In some instances, a smaller wound has an area of between 1 cm² and 1.6 cm². In some embodiments, larger wounds may also be treated without the central zinc gauze, particularly wounds without drainage, but not limited to such wounds. When the wound is sufficiently small, the wound can have little drainage, and zinc gauze 140 can be applied to the entire exposed area of the wound. Because of the minimal drainage observed in wounds of this size, there is reduced risk that drainage can impair healing. In some embodiments, once a wound treated by a method described in the present disclosure employing central drainage gauze and zinc gauze has been reduced to a surface area of less than about 1.6 sq. cm, the central drainage gauze can be omitted from the dressing. The zinc gauze can then be in contact with the entire exposed area of the wound.

Unlike current dressings for chronic wounds, such as venous ulcers, methods of the present disclosure do not require specialized medical knowledge or skill in order to effectively dress and treat a wound. The methods described herein can be easily performed at home. In some embodiments, the methods can be performed using separate materials, such as gauze suitable for use as central drainage gauze; a zinc gauze (e.g., Unna dressing) or a standard gauze and a zinc paste (e.g., zinc oxide), where the zinc past is applied to the gauze to produce a zinc gauze. Where the zinc gauze does not serve to hold the dressing in place, a wrap or adhesive strip can be used to retain the dressing in place. In other embodiments, the dressing components can be supplied in a more ready-to-use form, as defined in this description. In yet other embodiments, a medical professional can prepare the supplies for a patient in advance so that the patient can change their dressings at home. Where preparation of the wound prior to dressing is required, this can also be performed by a patient at home by, for example, wet-to-dry saline debridement before applying the dressing according the methods described in the present disclosure.

The methods provided herein often result in healing rates nearly twice those of other dressings. This fact, combined with the ability for patients to change dressings at home, can result in decreased medical office visits, increased compliance, and improved health. The inexpensive nature of the dressings used in the zinc rim protocol described herein and reduced medical office visits can also significantly reduce the cost of treating a chronic wound such as a venous ulcer or secondary intention wound.

In some embodiments, the methods provided herein can also include applying an antimicrobial agent or other agent to aid healing such as a preparation containing a cytokine such as platelet aggregating factor to the wound prior to applying the central drainage gauze 130 and zinc gauze 140 to the wound. This can help avoid, for example, bacterial growth in the wound, which can further slow or prevent healing. Any topical antimicrobial agent appropriate for use with wound dressings can be used. In one embodiment, the topical antimicrobial agent can be medical grade Manuka honey.

Other aspects provide wound dressings. In certain embodiments, the wound dressings can be used to dress chronic wounds, such as venous ulcers. The dressings can nearly double healing rates relative to other known dressing types (see, e.g., Examples 1 and 2). Referring to FIG. 2, a dressing of some embodiments includes central drainage gauze 230 and zinc gauze 240. Referring to FIG. 3, a dressing of other embodiments includes retention layer 350, zinc gauze 340, and central drainage gauze 330.

Figure 9:
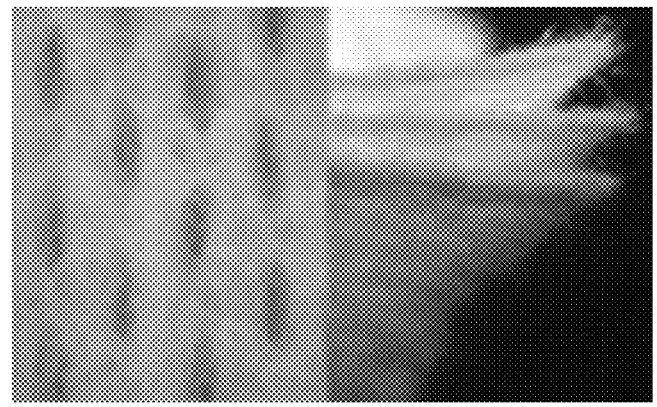
FIG. 9 is a photograph of one embodiment of gauze used as central drainage gauze according to one embodiment of the present disclosure.

In some embodiments, the central drainage gauze is a porous gauze capable of wicking excess exudate away from the central drainage zone of the wound (see, e.g., FIG. 9). In certain embodiments, the central drainage gauze has pores that are small enough to allow osmotic action, but large enough to allow direct pass-through drainage. A multi-ply gauze can be used for the central drainage gauze. In certain embodiments, a 3-ply porous gauze can be used. Such gauzes are known in the art. In a particular embodiment, 6-ply McKesson Performance Plus Gauze Drain Split Sponge is used, where the gauze in unfolded once to provide a 3-ply gauze. In certain embodiments, multiple layers of a single ply or multi-ply gauze can be used. For example, in certain embodiments, 10 layers of 3-ply McKesson Performance Plus Gauze Drain Split sponge can be used (see, e.g., FIGS. 15-19). Those of ordinary skill in the art will recognize that many different types of gauze may be used.

In some embodiments, the central drainage gauze is cut to or provided in a size that when placed in the central drainage zone of a wound, an exposed rim or periphery of the wound is left exposed. In certain embodiments, the central drainage gauze is cut to size or provided in a size that will leave a rim having a width of about 2 mm to about 10 mm when the central drainage gauze is placed in the central drainage zone. The rim can include all or a significant proportion of the peripheral healing zone. In some embodiments, the central drainage gauze is cut to or provided in a size that results in a rim of about 2 mm to about 4 mm. In a particular embodiment, the rim is about 2 mm to about 3 mm. In other embodiments, the central drainage gauze is cut to or provided in a size that results in a rim of about 4 mm to about 6 mm. In a particular embodiment, the rim is about 6 mm to about 8 mm. In yet another embodiment, the rim is about 3 mm to about 5 mm.

In certain embodiments, the zinc gauze is any gauze suitable to be infused, or saturated, with zinc. Any pharmaceutically acceptable form of zinc can be used to produce zinc gauze. In some embodiments, the zinc gauze is impregnated with zinc oxide, zinc sulfate, zinc pyrithione, or zinc gluconate. In a particular embodiment, the zinc gauze is zinc oxide. In some embodiments, an approximately central cutout, or fenestration, can be made in the zinc gauze.

In embodiments including a retention layer, the retention layer can be a wrap or an adhesive strip. A wrap can include, for example, a compression bandage, an elastic bandage, or a wrap dressing such as a roll of gauze. Any type of wrap capable of holding the dressing in place can be used. An adhesive strip can be, for example, medical tape or a dressing adhesive. The adhesive strip can be selected based on the desired properties of the dressing, such as breathability, water resistance, ease of removal, etc. Suitable retention layers are known in the art.

In some embodiments, the dimensions of the various gauzes can be adjusted or selected for a particular application. For example, most ulcers sizes can be covered by a 3.2 cm×4.4 cm section of gauze. In some embodiments, small ulcers can be dressed by an oval dressing of the present disclosure (see, e.g., FIG. 19). Many wounds are longer than they are wide (ratio of, for example, 4:3), and thus can be accommodated by an oval dressing arrangement, which can limit adhesive irritation when changing dressings. In some embodiments, the central drainage gauze 130 is an oval having a length-to-width ratio of, for example, 4:3 (see, e.g., FIG. 19). In other embodiments, the central drainage gauze 130 can be a rectangle having a length-to-width ratio of, for example, 4:3. In yet other embodiments, the central drainage gauze can be approximately circular or approximately square. In certain embodiments, central drainage gauze 130 is an oval having dimensions of about 3.545 cm×about 2.6625 cm, resulting in an area of approximately 9.4 cm$^2$, which is approximately 2 cm$^2$ in excess of the weighted average of the initial ulcer area for the studies cited in Table 2; and therefore is expected to cover over half of venous leg ulcers encountered.

In another embodiment, the central drainage gauze 130 is an oval with dimensions of about 3.2 cm×about 4.4 cm resulting in an area of approximately 14.1 cm$^2$ (see, e.g., FIGS. 15-18). In some embodiments, the larger central drainage gauze 130 and necessarily larger zinc gauze 140 require a greater retention layer surface (e.g., adhesive surface) to achieve adequate retention.

Other embodiments provided herein provide a wound dressing including dressing including a zinc gauze configured to occupy an entirety of an exposed wound, and a retention layer configured to retain the zinc gauze on the exposed wound. The zinc gauze can be any zinc gauze described by the present disclosure. The retention layer can be any retention layer described in the present disclosure. In certain embodiments, the retention layer is not a wrap.

Various changes and modifications can be made to the steps of the zinc rim protocol and associated materials described herein to accommodate different scenarios and wound requirements without departing from the concept of central drainage gauze in contact with a central drainage zone and zinc gauze in contact with a peripheral healing zone. For example, in some embodiments, especially for smaller wounds, but not limited to such wounds, wound dressings and wound dressing protocols may or may not include a central drainage zone, and instead may include a uniform layer of zinc gauze and an adhesive layer (see e.g. FIG. 23B).

Figure 4:
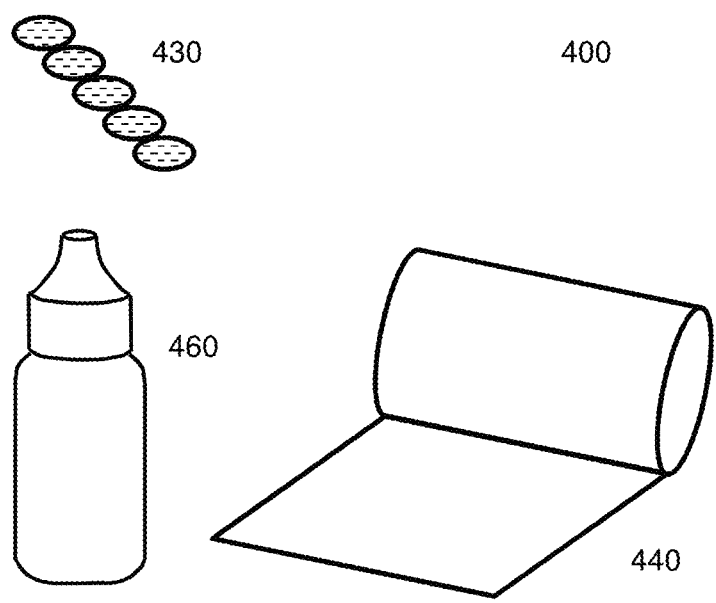
FIG. 4 is a schematic diagram representing a wound dressing kit according to one embodiment of the present disclosure.

Some aspects provide wound dressing kits. Referring to FIG. 4, embodiments of some wound dressing kits include central drainage gauze 430, zinc gauze wrap 440, and physiological solution 460. In certain embodiments, central gauze 430 is supplied in one or several sizes. If supplied in a single size, central gauze 430 can be cut to the appropriate size to produce an adequately wide, exposed wound periphery when placed in the central drainage zone. If supplied in several sizes, central drainage gauze having a size that would leave an adequately wide, exposed wound periphery can be selected. Alternatively, central drainage gauze having the closest appropriate size can be selected and cut to produce appropriately sized gauze. The gauze wrap can be any gauze wrap impregnated with, or to which has been applied, a pharmaceutically acceptable form of zinc, such as zinc oxide. In a particular embodiment, the zinc gauze wrap is an Unna boot dressing. The physiological solution is used to saturate the central drainage gauze, and can be any physiological solution known in the art. In some embodiments, the physiological solution is a saline solution. In particular embodiments, the physiological solution is a 0.9% saline solution.

Figure 5:
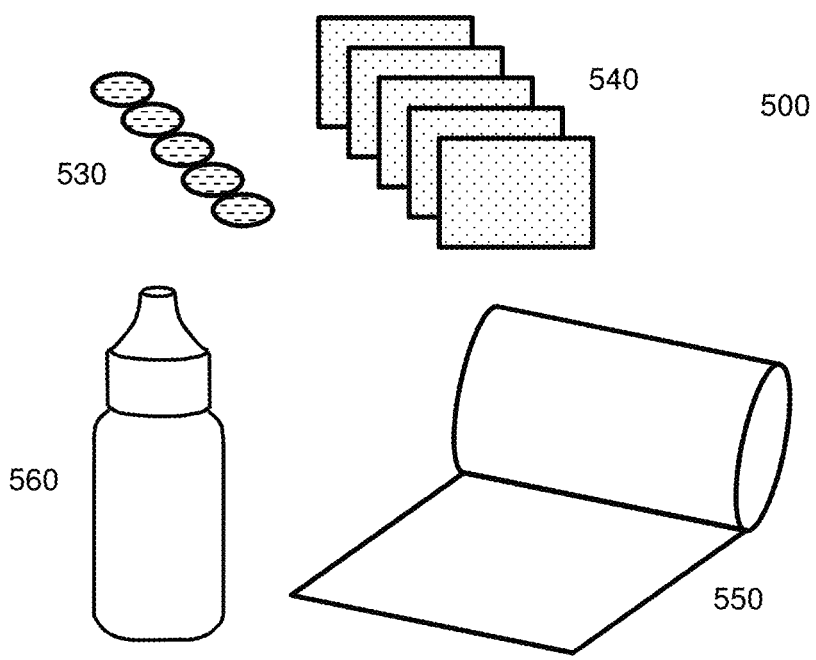
FIG. 5 is a schematic diagram representing a wound dressing kit according to one embodiment of the present disclosure.

Referring to FIG. 5, embodiments of some wound dressing kits include central drainage gauze 530, zinc gauze 540, retention layer 550, and physiological solution 560. Central gauze and physiological solution described in the embodiment of claim FIG. 5 are the same as those provided in the embodiment of FIG. 4. The zinc gauze can be any gauze containing a pharmaceutically acceptable form of zinc, such as zinc oxide. The zinc gauze is provided in a size sufficient to fully cover a wound. The zinc gauze can extend beyond the periphery of the wound. The retention layer 550 can be a wrap or an adhesive strip. A wrap can include, for example, a compression bandage, an elastic bandage, or a wrap dressing such as a roll of gauze. Any type of wrap capable of holding the dressing in place can be used. An adhesive strip can be, for example, medical tape or a dressing adhesive. The adhesive strip can be selected based on the desired properties of the dressing, such as breathability, water resistance, ease of removal, etc. Suitable retention layers are known in the art. The physiological solution is the same as that described for the embodiment of FIG. 4.

Figure 6:
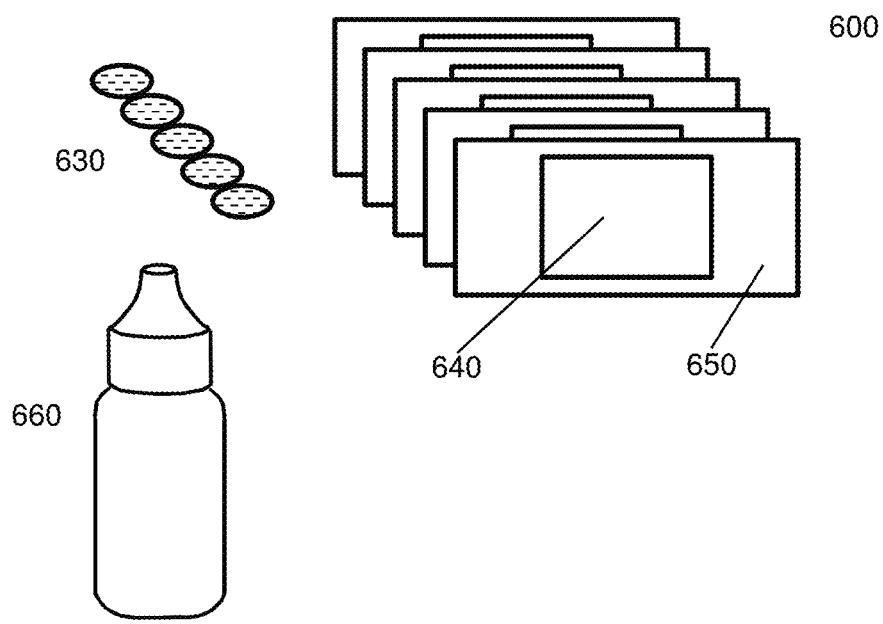
FIG. 6 is a schematic diagram representing a wound dressing kit according to one embodiment of the present disclosure.

Referring to FIG. 6, embodiments of some wound dressing kits include central drainage gauze 530, zinc gauze 540 affixed to retention layer 550, and physiological solution 560. Central gauze and physiological solution described in the embodiment of claim FIG. 6 are the same as provided in the embodiment of FIG. 4. Zinc gauze 540 is similar to that described in the embodiment of FIG. 5, with the difference being that it is affixed to retention layer 550, where retention layer 550 is an adhesive strip. In this configuration, the kit resembles a standard household bandage with the addition of the central drainage gauze and physiological solution. A user of such a kit prepares the wound and central drainage gauze appropriately, and then applies the combination of zinc gauze 540 and retention layer 550 over the wound in which the central drainage gauze was placed. The result is a wound having central drainage gauze in contact with the central drainage zone and zinc gauze in contact with the peripheral healing zone.

Any of the kits described herein can also include additional gauze to be used as dry, absorbent gauze for use as described herein. This additional gauze can be the same type of gauze used for central drainage gauze, or another suitably absorbent gauze. The kits described herein can also include additional items including, but not limited to, examination gloves, scissors (to cut central drainage gauze), debridement scissors, additional physiological solution for use in debridement, one or more saturation trays for saturating central drainage gauze prior to application to a wound central drainage zone, and an instruction sheet.

Figure 23A:
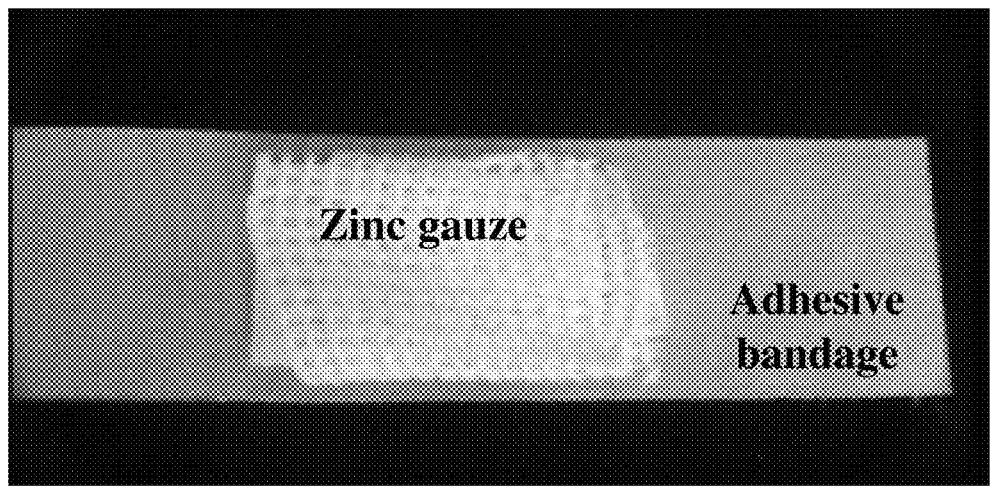
FIGS. 23A-23B are photographs of wound dressings according to embodiments of the present disclosure.
Figure 23B:

In certain embodiments, a kit can include a section of zinc gauze and a retention layer (see, e.g., FIG. 23A-23B). In one embodiment, the zinc gauze can be affixed to the retention layer (see, e.g., FIG. 23A-23B).

Any of the kits described in the present disclosure can also include a topical antimicrobial agent suitable for use with a wound dressing, and/or other agent to aid healing such as a preparation containing a cytokine such as platelet aggregating factor or Manuka honey.

Various changes and modifications can be made to the steps of the zinc rim protocol and associated materials described herein to accommodate different scenarios and wound requirements without departing from the concept of central drainage gauze in contact with a central drainage zone, in some embodiments, and zinc gauze in contact with a peripheral healing zone.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to adapt it to various usages and conditions Example 1—Treatment of Venous Ulcers with Zinc Rim Protocol In an exemplary study, venous leg ulcers of three patients were treated using the zinc rim protocol. The ulcers healed at an average healing rate of 46.1% per week, which is considerably greater than with other dressing protocols (Table 2).

Case 1

Figure 10A:
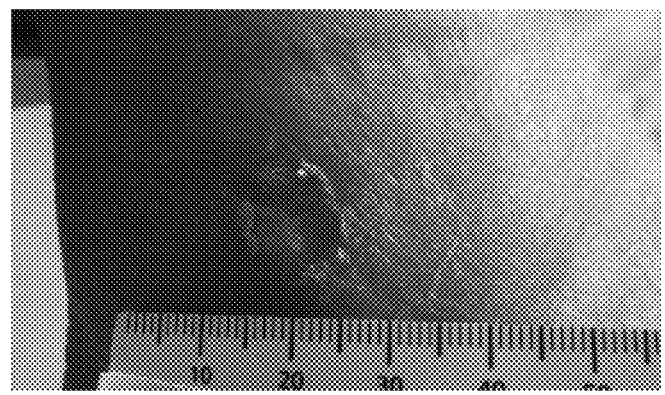
FIGS. 10A-10B are photographs of the wound in Case 1 before (10A) and after (10B) treatment with the zinc rim protocol according to one embodiment of the present disclosure.
Figure 10B:
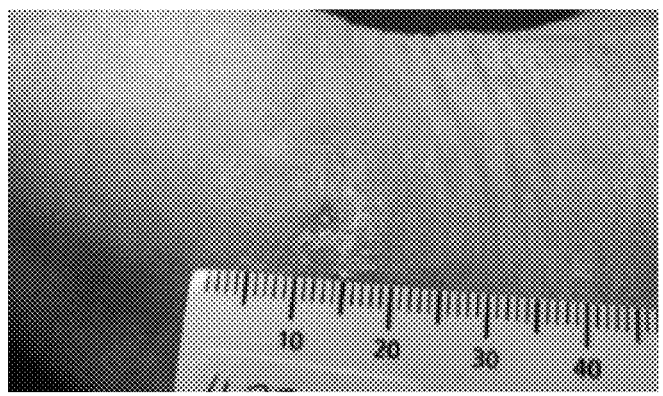

A 79-year-old female developed an ulcer on the lateral right ankle after minor trauma four months previously. There was no prior treatment. She was an everyday smoker and had a history of hypertension. She had no history of diabetes. At the initial visit both lower extremities had 2+ pitting edema. The ulcer had an exudative depressed central area of 0.13 cm$^2$ (FIG. 10A). Unna boot therapy with short-stretch dressing was begun, including the saline-soaked central gauze per study protocol. She requested to change her own dressing at home; she was taught the Unna dressing technique and her wrapping technique was found to be satisfactory. She changed the saline gauze and Unna boot every two days. After ten days of treatment, the ulcer had decreased in size from 0.13 cm$^2$ to 0.037 cm$^2$ (FIG. 10B). The ulcer was sufficiently healed that the Unna boot and gauze dressings were discontinued and the patient was discharged. Compression stockings were advised. The ulcer healed shortly after clinic discharge and was still healed on follow-up visit 4 months later.

Case 2

Figure 11A:
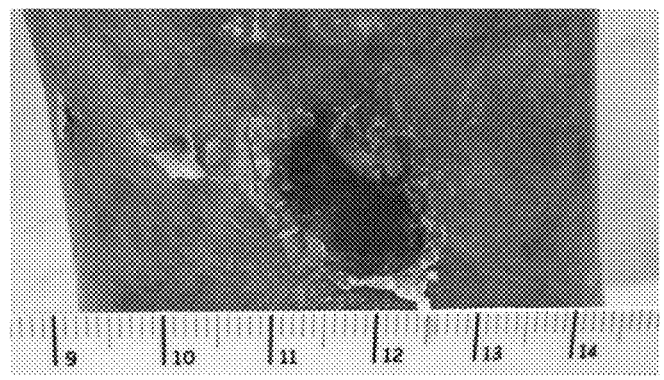
FIGS. 11A-11C are photographs of the wound in Case 2 before treatment with the zinc rim protocol according to one embodiment of the present disclosure (11A), at discharge (11B), and at follow-up (11C).
Figure 11B:
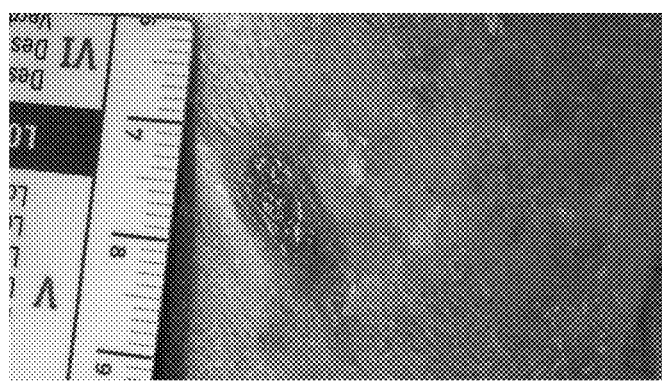
Figure 11C:
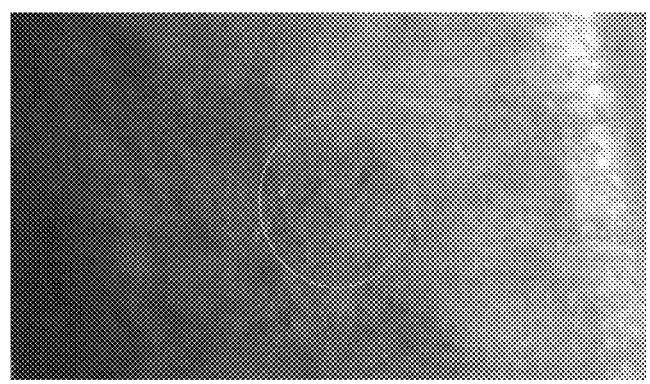

An 82-year-old female with hypertension had a painful ulcer on her leg for nine months. She had a normal BMI and no history of diabetes or smoking. A wound care clinic had employed Unna boots and debridement over the nine-month period. During this period the ulcer healed and recurred (FIG. 11A). Examination showed trace edema and no apparent infection. Three-layer Unna boot therapy with saline-soaked gauze per study protocol was begun with 2-day application cycles. Her husband was taught the Unna boot technique; his Unna boot wrapping technique was found to be satisfactory. Saline soaks for a duration of 20 minutes were used at the time of dressing changes. After 12 days her ulcer had reduced in size to 0.669 cm$^2$ (FIG. 11B). She was discharged with instructions to continue the 2-day application cycles as was done in the clinic until the ulcer was healed. She continued the zinc gauze for a period of less than two weeks and thereafter used only compression. The healed ulcer showed no sign of recurrence four months later. The wound was healed on examination 5 months later (FIG. 11C).

Case 3

Figure 12A:
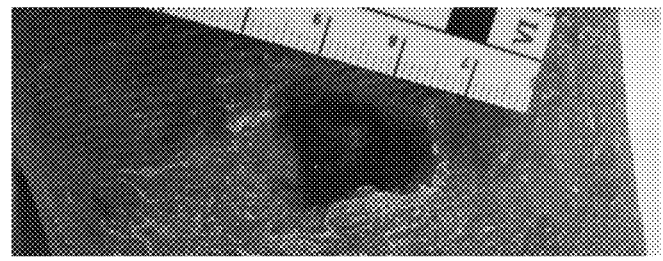
FIGS. 12A-12C are photographs of the wound in Case 3 before treatment with the zinc rim protocol according to one embodiment of the present disclosure (12A), at discharge (12B), and at follow-up (12C).
Figure 12B:
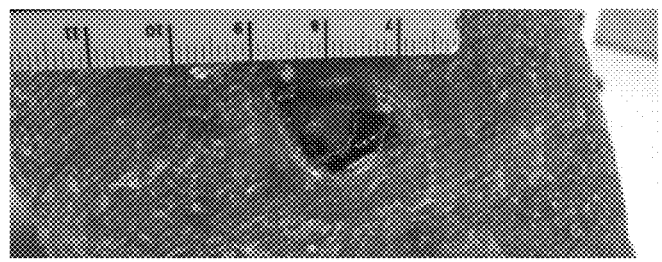
Figure 12C:
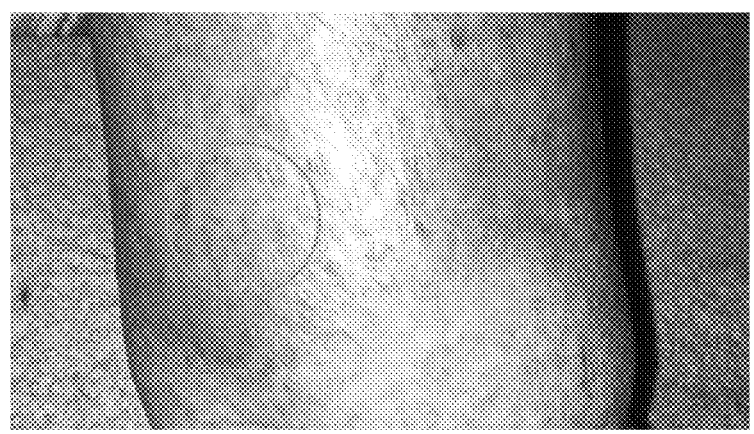

An 88-year-old female patient was morbidly obese (BMI 51.34) and had a history of hypertension; she had no history of diabetes or smoking. She reported a 3-week history of a non-painful leg ulcer (FIG. 12A). The affected leg had weeping 3+ edema. Three-layer Unna boot therapy with saline-soaked gauze per protocol was begun. Unna boots were changed twice weekly in the clinic. To accommodate heavy drainage from the ulcer, a 2 cm thick 3×3 inch gauze pad was placed outside the Unna dressing and under the elastic bandage to absorb drainage. She began 300 mg of horse chestnut seed extract oral supplement twice daily for the duration of the study treatment to aid in healing. Within 10 days, the open ulcer area had decreased from 2.08 cm$^2$ to 0.30 cm$^2$ (FIG. 12B). The patient was discharged from clinic and instructed to apply Unna dressing squares under adhesive bandages, per protocol. Follow-up examination six months later, when she returned for treatment of a new ulcer, showed no recurrence of the original ulcer (FIG. 12C).

Results and Discussion of Cases 1-3

Ulcer sizes, duration, and wound healing rates for cases 1-3 are shown in Table 1.

TABLE 1

Initial and final ulcer sizes, ulcer duration, and weekly healing rates of venous ulcers treated with the zinc rim protocol described herein.

| Case | Initial Ulcer Size | Final Ulcer Size | Unna Boot Duration | Wound Healing cm$^2$/Week |
|---|---|---|---|---|
| Case 1 | .134 cm$^2$ | .037 cm$^2$ | 10 days | 50.7% |
| Case 2 | 1.279 cm$^2$ | .669 cm$^2$ | 12 days | 27.8% |
| Case 3 | 2.078 cm$^2$ | .304 cm$^2$ | 10 days | 59.8% |
| Average | 1.164 cm$^2$ | .337 cm$^2$ | 10.7 days | 46.1% |

Representative studies showing leg ulcer healing rates for ulcer treatment methods are listed in Table 2. The weekly wound healing rates in these studies range from 3.5% to 20.5%. In only one study were all the ulcers healed at the study conclusion. The average weekly wound healing rate for the three cases treated with the central gauze technique was 46.1%.

TABLE 2

Healing rates of venous ulcers with various treatment protocols.

| Author | Treatment Method | Number of Patients | Duration | Average Initial Ulcer Size | Wound Healing Rate per Week | Ulcers Healed |
|---|---|---|---|---|---|---|
| Backhouse et al 1987 | Compression | 28 | 12 weeks | 3.4 cm$^2$ | 20.5% | 22/28 (78%) |
| | Hydrocolloid | 28 | 12 weeks | 3.4 cm$^2$ | 18% | 21/28 (75%) |
| Cordts et al 1992 | Unna boot | 14 | 12 weeks | 6.0 cm$^2$ | 5% | 6/14 (43%) |
| | Duoderm | 16 | 12 weeks | 9.1 cm$^2$ | 7.5% | 8/16 (50%) |
| Luz et al 2013 | Unna boot | 32 | 8/12 weeks | 15.3 cm$^2$ | 3.7-4.2% | N/A |
| | Simple bandage | 11 | 8/12 weeks | 28.2 cm$^2$ | 3.6% | N/A |
| Limova 2003 | Alginate (Tegagen, Sorbsan) | 19 | 6 weeks | 6.9 cm$^2$-8.5 cm$^2$ | 4.9%-5.6% | 0%-22% |
| Samuels et al 2013 | Ultrasound (20 kHz for 15 minutes) | 5 | Varied | 4.8 cm$^2$ | 12% | 5/5 (100%) |
| | Ultrasound (20 kHz for 45 minutes) | 5 | Varied | N/A | 7% | 1/5 (20%) |
| | Ultrasound (100 kHz for 15 minutes) | 5 | Varied | N/A | 7% | 2/5 (40%) |
| Hussain 2015 | Nonadherent Ultra dressings | 12 | Varied | 5.47 cm$^2$ | 12.2% | 7/12 (58%) |
| Wtd. Average* | | | | 7.4 cm$^2$ | 10.3% | |

*1. Initial size weighted equation. Luz series is excluded because of outlier sizes of venous ulcers in developing country (Brazil): (56*3.4 + 14*6 + 16*9.1 + 19*7.7 + 5*4.8)/110 = 5.4 cm$^2$
2. Healing rate/week weighted equation, excluding Luz series from Brazil: (28*20.5 + 28*18 + 14*5 + 16*7.5 + 32*3.95 + 11*3.6 + 19*5.35 + 5*12 + 5*5 + 5*7 + 12*12.2)/175 = 10.3%/week
3. An ellipse with dimensions (twice the axis) 3.545 and 2.6625 has area 7.4 cm$^2$ and will therefore cover over half of venous ulcers.

The dressing change procedure with the central gauze entails only the application of saline-soaked gauze to the central part of ulcer. Once the ulcer had sufficiently healed, the home dressing change involves only the application of the Unna gauze to the ulcer. Most patients need professional help with the Unna boot; therefore they need to be followed in the clinic. In contrast, most patients can manage the home phase of the zinc rim protocol used in this study, which involves applying the Unna gauze under an adhesive dressing and then applying elastic compression.

Moisture Management with the Zinc Rim Protocol

Moisture in the ulcer environment is favorable; excess drainage that pools under an occlusive dressing is unfavorable. Drainage is maximum at the ulcer center, and minimum at the ulcer periphery, where healing occurs. An Unna boot is advantageous for rapid healing because the zinc-oxide impregnated gauze is in contact with the ulcer periphery. With the unmodified Unna dressing, the potential healing advantage of zinc oxide is diminished because of excess moisture, sometimes visible on clinic visits where it has leaked out of the Unna boot. The two-zone model depicted in FIGS. 1A-1B and described herein can explain how modification of the Unna boot to absorb exudate from the central zone can significantly improve the healing rate. The saline-soaked gauze in the center promotes wicking away of excess drainage. The configuration of the central gauze employed here can allow increased drainage. The dimensions of the elliptical openings are small enough to allow osmotic action and large enough to allow for direct pass-through of excess drainage. For heavy drainage, as we observed in Case 3, a 2 cm thick pad of standard 3×3 or 4×4 gauze may be placed outside the Unna wrap.

Accelerated Healing with Zinc Oxide at the Ulcer Rim Via Unna Boot

The study's zinc rim protocol is targeted to two ulcer zones: a central zone covered with a dressing of gauze and saline and a peripheral healing zone covered with Unna dressing: gauze and zinc oxide. When healing is sufficient and drainage is minimal (i.e., wound reduced to a size below approximately 1 cm in greatest diameter or 1.6 cm$^2$ area), the central saline-soaked gauze many be eliminated, applying only zinc gauze.

Materials and Methods for Cases 1-3
Zinc Rim Protocol

Figure 7:
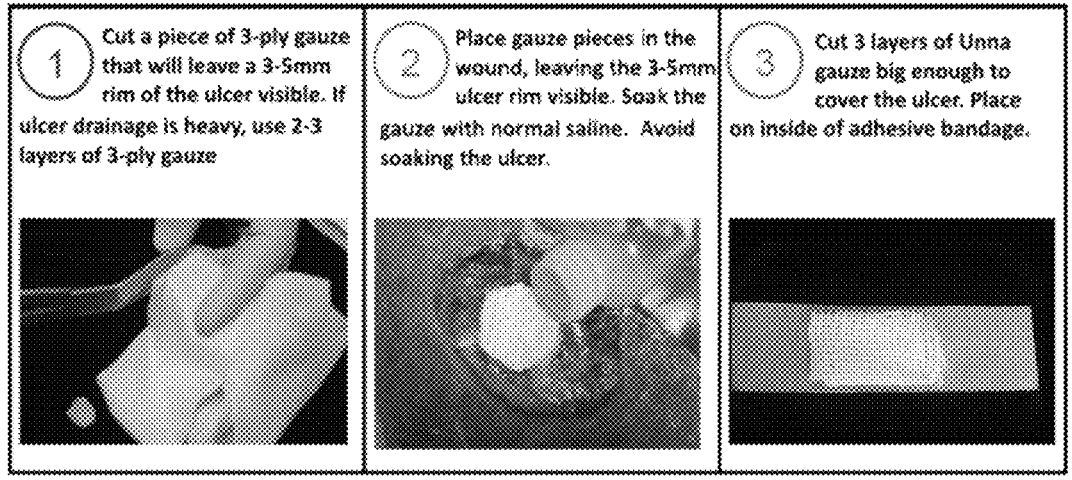
FIG. 7 is a flow diagram demonstrating some of the steps of a method according to one embodiment of the present disclosure.
Figure 8:
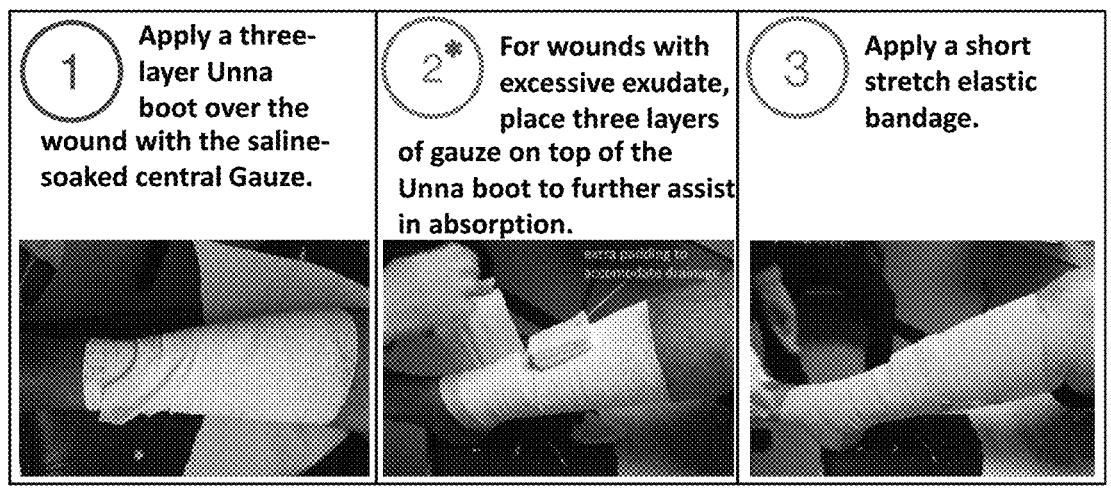
FIG. 8 is a flow diagram demonstrating some of the steps according to one embodiment of the present disclosure.

A sheet of 6-ply McKesson Performance Plus Gauze Drain Split Sponge (McKesson Corporation, San Francisco, Calif.) was unfolded so that the gauze was three layers thick rather than six. Comparable porous gauze could be similarly used. The gauze was cut to nearly cover an ulcer or wound, leaving about a 2 mm-10 mm rim of the ulcer exposed around the gauze piece (FIG. 1A, FIG. 7). The gauze piece was soaked with 0.9% saline solution. The width of the exposed ulcer can be adjustable to provide desired drainage. If the ulcer has little or no exudate, the width of the ulcer rim surrounding the gauze can be approximately 5 mm-10 mm. With increased exudate, this width can be reduced to approximately 2 mm-3 mm. Ulcers with excessive exudate had a second or third 3-layer piece of dry gauze applied on top of the saline-soaked piece (FIG. 8).

After placing the saline-soaked gauze piece approximately centrally inside the wound, a three-layer Unna boot was applied. The Unna dressing (Repara, PSS World Medical, Jacksonville, Fla.) was followed by a single layer of gauze wrap, and finally short stretch elastic bandage (Comprilan, BSN Medical, Hamburg, Germany). Using this method, only a rim of zinc oxide came into direct contact with the wound, different from the full contact with the ulcer that a standard Unna boot provides. The tri-layer configuration of the porous McKesson gauze was effective in absorbing the drainage in the central ulcer area. The elliptical pore design and basic tri-layer configuration are shown in FIG. 9

Experimental Study Protocol.

Undressed ulcers were photographed before and after treatment to record size. A measuring ruler was included in each photograph to accurately determine the area of the ulcer. The area of the best fit ellipse was calculated using a standard formula after determining the major and minor axes of the ellipse. Healing was defined as epithelialization, with or without thing crust, with no ulcer area present. The ulcer area was defined as the area with visible moist dermis and no epidermis. This are of visible moist dermis was photographed at each visit. The patient was discharged from the clinic with compression dressings. For patients with visible ulcer area at the time of discharge, as in Cases 2 and 3, the patient was provided with pieces of Unna dressing cut to cover the ulcer and place under adhesive bandages (Coverlet Adhesive Bandages, Beiersdorf Inc, Wilton Conn.).

Example 2—Treatment of Additional Wounds by Zinc Rim Technique

In a second exemplary study, three secondary intention wounds of various causes were healed by the zinc rim protocol. The average healing rate of the three wounds was 21.7 mm$^2$/day. This compares favorably to standard healing rate in the range of 14 mm$^2$/day (Gohari et al., Dermatol Surg. 2002 December; 28(12):1107-14. PMID:12472488).

Case 4

Figure 13A:
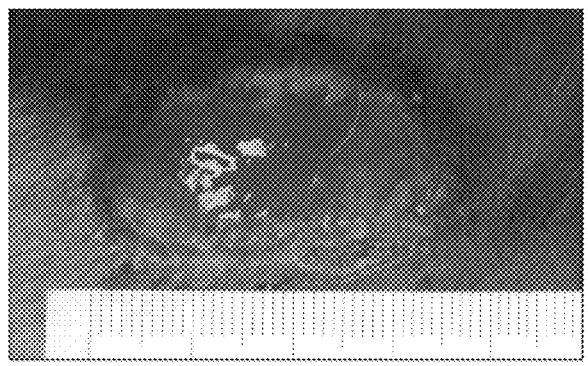
FIGS. 13A-13B are photographs of the wound in Case 4 before treatment with the zinc rim protocol according to one embodiment of the present disclosure (13A) and at discharge (13B).
Figure 13B:
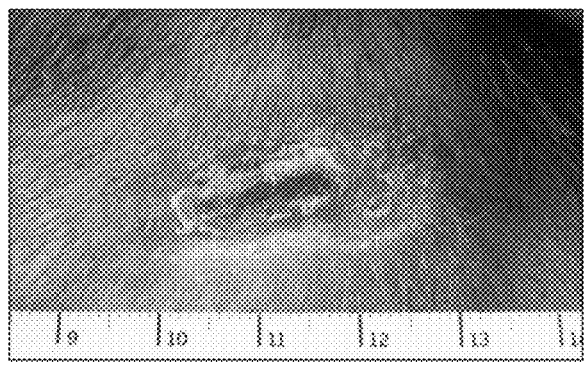

A 53-year-old male cigarette smoker presented with a 3.3 cm (greatest dimension) basal cell carcinoma on the posterior scalp. The lesion was treated with curettage. The post-operative wound (FIG. 13A), area 4.41 cm$^2$; produced excessive clear exudate. The zinc rim protocol dressing was begun with imiquimod applied 5×/week. After six days the open wound decreased from 4.41 cm$^2$, FIG. 2a, to 1.59 cm$^2$. After another two weeks it further decreased to 0.12 cm$^2$ (FIG. 13B). The patient was discharged from the clinic with instructions to leave the wound open to air.

Case 5

Figure 14A:
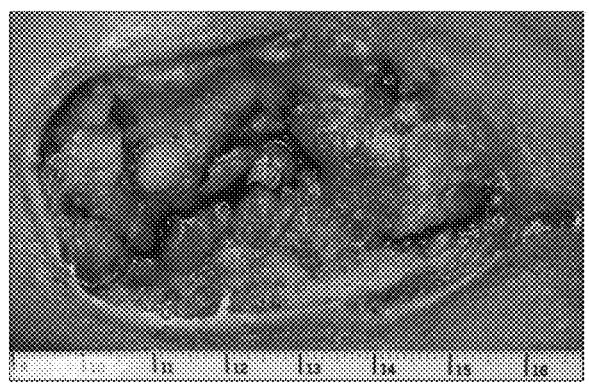
FIGS. 14A-14B are photographs of the wound in Case 5 before treatment with the zinc rim protocol according to one embodiment of the present disclosure (14A) and at discharge (14B).
Figure 14B:
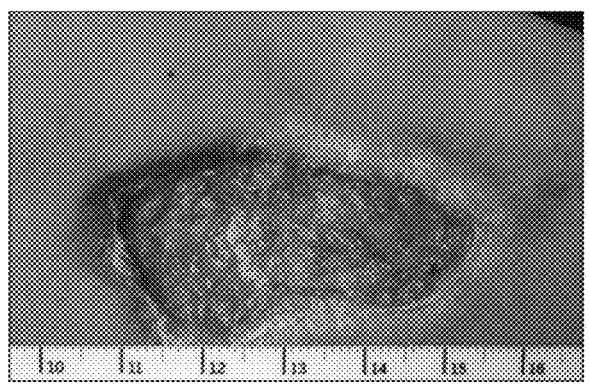

A 28-year-old female presented with dermonecrosis and a 24-hour history of throbbing pain in the right arm. The wound was scored as a probable brown recluse spider bite by Rader criteria. Necrotic tissue was debrided by curettage, leaving a 14.61 cm$^2$ open wound (FIG. 14A). After three weeks of treatment with the zinc rim protocol dressing, the wound area had decreased to 7.67 cm$^2$ (FIG. 14B).

Case 6

A 54-year-old female patient developed a Stage 1b melanoma on her right anterior thigh. After excision with 1 cm margins and intermediate closure, the wound dehisced on post-surgical day 5. After repair, the wound dehisced a second time, developed a *Staphylococcus aureus* infection, and was treated with oral antibiotic and wet-to-dry dressing changes twice daily for three days. Zinc rim protocol dressings were begun, with wet-to-dry dressings between dressing changes until the area was healed completely. The 7.85 cm$^2$ wound was healed in 53 days, for a healing rate of 14.8 mm$^2$/day.

Results and Discussion of Cases 4-6

Three patients had wounds that healed by secondary intention using a targeted zone healing method, with zinc oxide gauze in the peripheral zone and drainage control in the central zone. The post-BCC scalp wound healed at a rate of 21.5 mm$^2$/day; the spider bite wound on the arm healed at a rate of 28.9 mm$^2$/day; and the dehisced surgical wound healed at a rate of 14.8 mm$^2$/day, for an average healing rate of 21.7 mm$^2$/day.

Materials and Methods for Cases 4-6
Zinc Rim Protocol 6-ply McKesson Performance Plus Gauze Drain Split Sponge (McKesson, San Francisco, Calif.) was unfolded to obtain 3-ply gauze. The gauze was then cut to leave a 3 mm-5 mm rim of the ulcer exposed around the gauze (see, e.g., FIG. 7). The gauze was soaked with 0.9% saline solution.

The ulcer area was covered with 3 layers of Unna gauze (Repara, PSS World Medical, Jacksonville, Fla.) overlapping normal skin (FIG. 1B). Telfa dressing (Medline, Kansas City, Mo.) was cut to cover the Unna gauze and secured with adhesive tape.

If the ulcer had little or no exudate, the width of the ulcer rim surrounding the gauze was about 5 mm; for heavy exudate, the rim width was about 3 mm. For ulcers with excessive exudate, a second or third 3-ply gauze layer was added over the saline-soaked piece. For heavy drainage, wet-to-dry 0.9% saline dressings were used before the new dressing is applied. Wet-to-dry saline dressings are kept on the wound until the dressing is dry, then removed. The time to dry was approximately two hours. For moderate drainage, 0.9% saline soaks were applied for 20 minutes. For treatment after skin cancer therapy, a pinhead amount of imiquimod 5% cream was applied to the lesion under the central gauze.

The ulcer area was covered with 3 layers of Unna gauze (Repara, PSS World Medical, Jacksonville, Fla.) overlapping normal skin (FIG. 1B). Telfa dressing (Medline, Kansas City, Mo.) was cut to cover the Unna gauze and secured with adhesive tape.

If the ulcer has little or no exudate, the width of the ulcer rim surrounding the gauze was about 5 mm; for heavy exudate, the rim width was about 3 mm. For ulcers with excessive exudate, a second or third 3-ply gauze layer was added over the saline-soaked piece. For heavy drainage, wet-to-dry 0.9% saline dressings were used before the new dressing is applied; for moderate drainage, 0.9% saline soaks were applied for 20 minutes. For treatment after skin cancer therapy, a pinhead amount of imiquimod 5% cream was applied to the lesion under the central gauze.

Undressed ulcers were photographed at dressing changes; a scale was included in each photograph. The ulcer area was calculated by the best-fit ellipse method, including only the area of the ulcer lacking epidermis.

Example 3—Zinc Rim Dressings and Zinc Rim Dressing Kits

Various exemplary zinc rim dressings are provided in the following examples.

Figure 15:
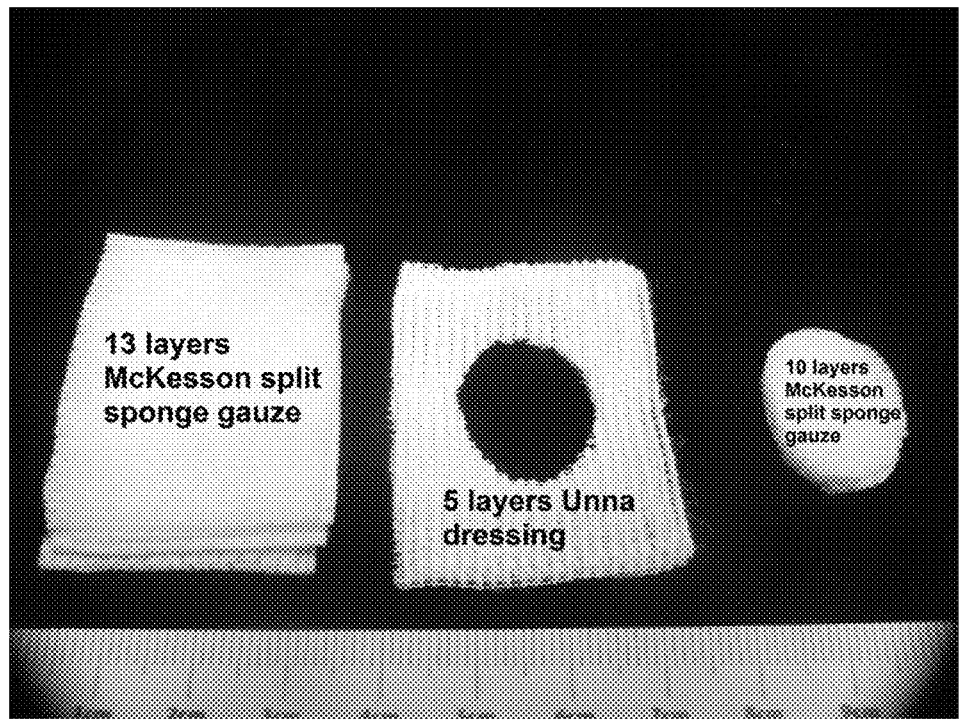
FIG. 15 is a photograph of examples of gauze used in a wound dressing according to one embodiment of the present disclosure.

Referring to FIG. 15, the photograph illustrates various types of gauze useful to dress a wound according to a method of the present disclosure. The gauze can be arranged into a dressing, or included in a dressing kit. From left to right in the photograph: 13 layers McKesson split sponge gauze, 5 layers Unna dressing, 10 layers McKesson split sponge gauze. Each layer of McKesson gauze is a compound triple layer (see, e.g., FIG. 9 and FIG. 16 inset). Dimensions and number of layers of gauze and zinc gauze may be modified to accomplish competing needs of capturing drainage and keeping dressing attached to skin.

Referring to FIG. 16, the photograph illustrates the gauze of FIG. 15, but provides examples of dimensions for the various types of gauze. The extra layers of dry gauze (13 layers of McKesson split sponge gauze) has dimensions of 3.1×4.4 cm. The Unna gauze had outer dimensions of 3.2×4.4 cm, with a central oval cutout having dimensions of 1.6×2.2 cm. The central drainage gauze (10 layers of McKesson split sponge gauze) has dimensions of 1.6×2.2 cm. An ulcer up to 14 cm$^2$ can be dressed with a dressing made using gauze of these dimensions.

Figure 17:
FIG. 17 is a photograph of a wound dressing according to one embodiment of the present disclosure.
Figure 18:
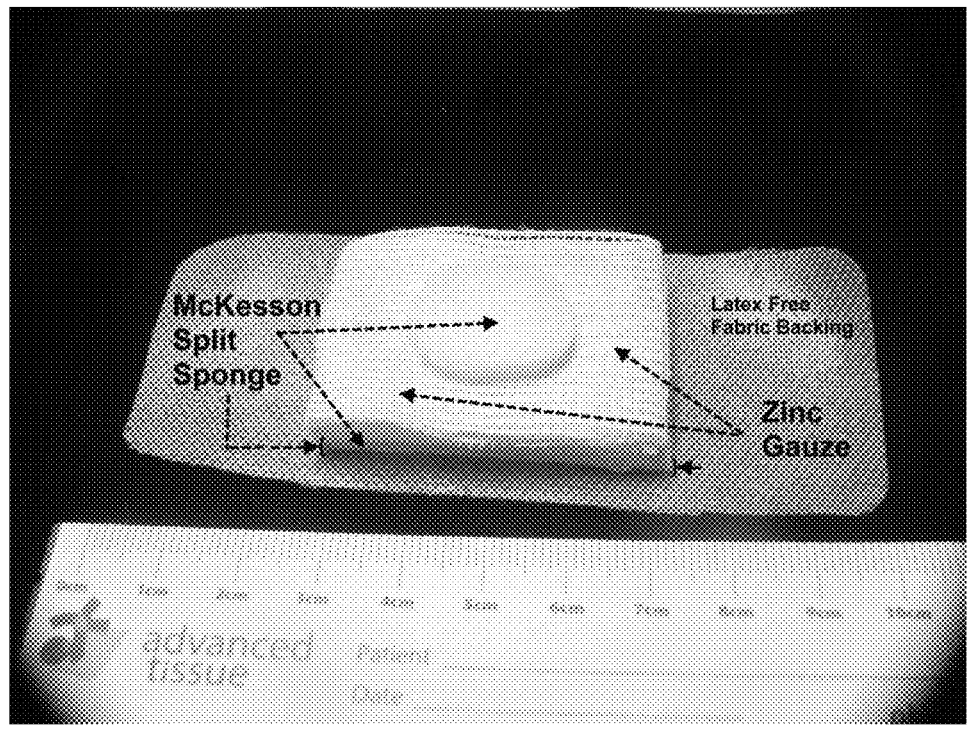
FIG. 18 is a labeled photograph of a wound dressing according to one embodiment of the present disclosure.

Referring to FIGS. 17 and 18, the photographs illustrates an assembled zinc rim wound dressing, including a latex-free adhesive fabric backing (retention layer), 13 layers of McKesson split sponge gauze (extra layers of dry gauze), 5 layers of Unna gauze and 10 layers of McKesson split sponge to be used as central drainage gauze.

Figure 19:
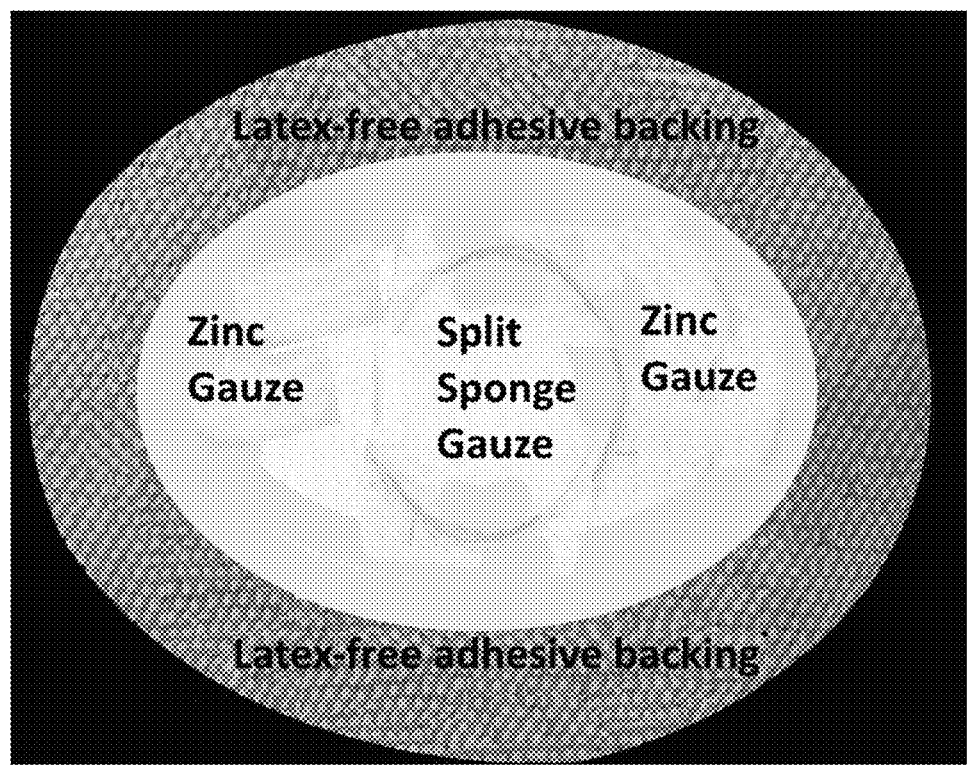
FIG. 19 is a labeled photograph of a wound dressing according to one embodiment of the present disclosure.

Referring to FIG. 19, the photograph illustrates an assembled oval zinc rim dressing including a latex-free adhesive fabric backing (retention layer), Unna gauze, and split sponge gauze to be used as central drainage gauze. The oval configuration can help to minimize irritation caused by the adhesive when changing the dressing.

Example 4—Additional Cases Using Zinc Rim Protocol

Example 4 provides two additional exemplary cases of skin wounds treated with the methods described in the present disclosure.

Case 7

Figure 20:
FIG. 20 is a photograph of leg of patient presenting with multiple non-healing diabetic venous ulcers prior to before treatment with the zinc rim protocol according to one embodiment of the present disclosure.
Figure 21A:
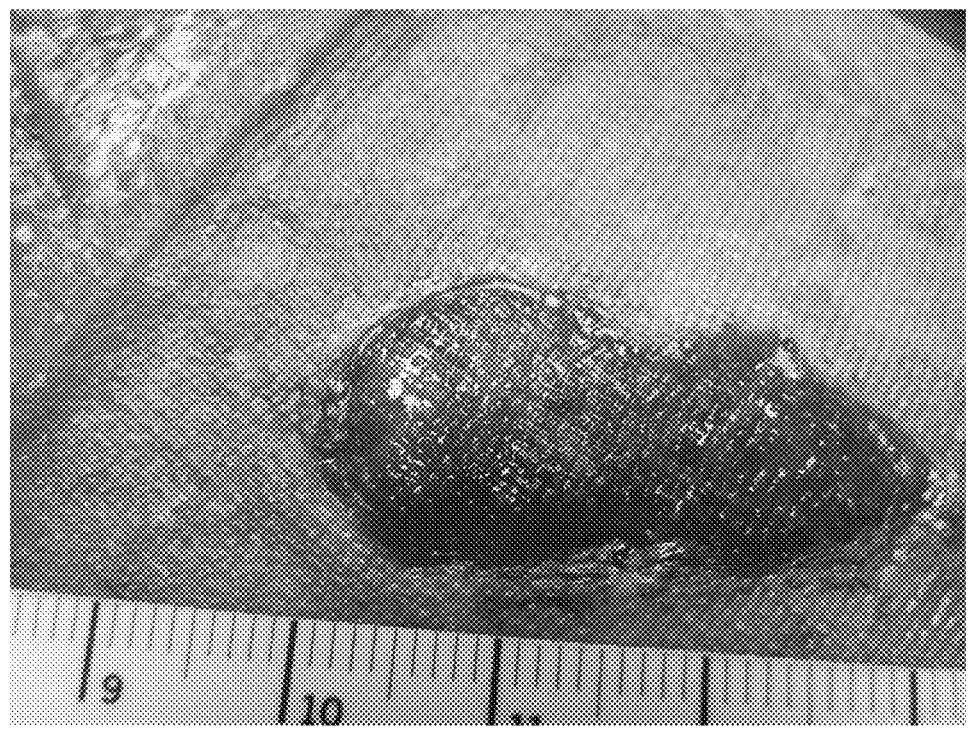
FIGS. 21A-21C are photographs of the ulcer appearing to the left (toward knee) of FIG. 20 at day 0 (FIG. 21A) and day 15 (FIG. 21B) after treatment with the zinc rim protocol according to one embodiment of the present disclosure, and at follow-up at day 133 (FIG. 21C).
Figure 21B:
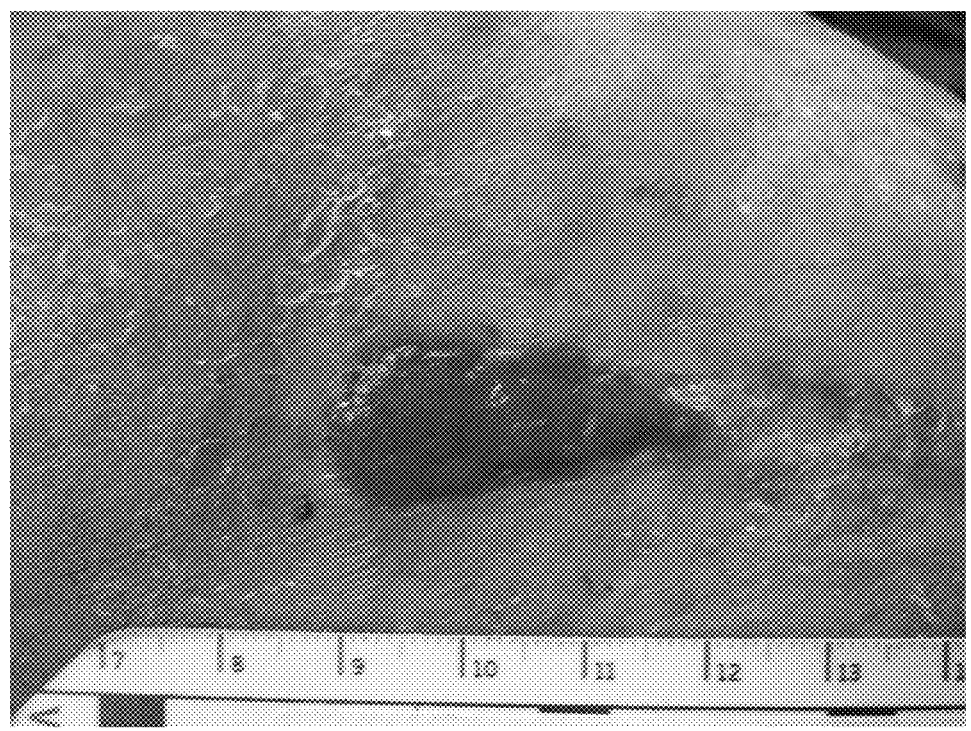
Figure 21C:
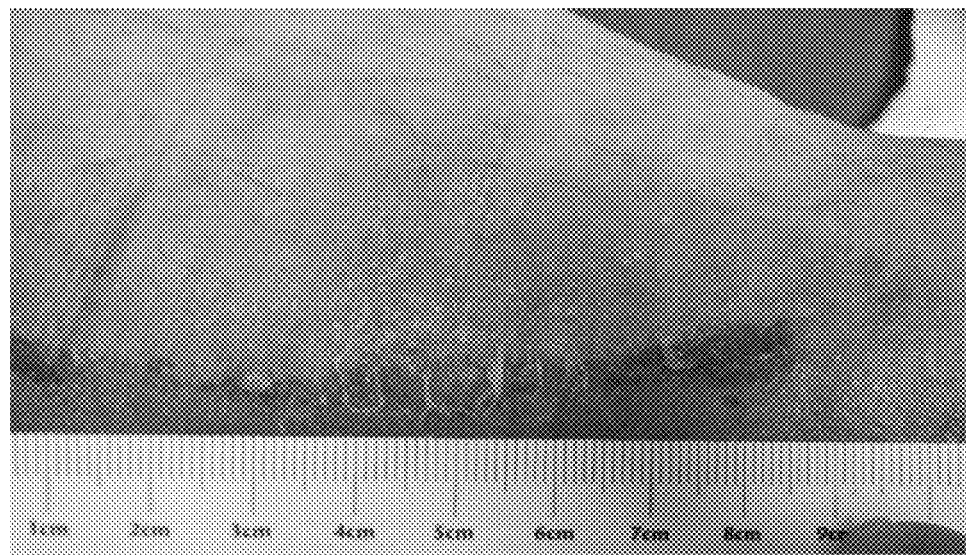

FIG. 20 depicts the leg of a 63-year-old male with insulin-dependent diabetes and over one year of Unna boot therapy with multiple non-healing ulcers. The photograph was taken Mar. 24, 2016, and depicts an overview of the left leg, medial pretibial area, before use of a zinc rim protocol. The zinc rim protocol was used to treat the ulcers. FIGS. 21A-C depict healing of the ulcer appearing in FIG. 20 toward the patient's knee before beginning the zinc rim protocol (FIG. 21A; Mar. 24, 2016), 15 days after beginning the zinc rim protocol (FIG. 21B; Apr. 8, 2016, and at follow-up 133 days after beginning the zinc rim protocol (FIG. 21C).

Case 8

Figure 22A:
FIGS. 22A-22B are photographs of a wound present for over two months in a patient without adverse healing factors at day 0 (FIG. 22A) and day 10 (FIG. 22B) after treatment with the zinc rim protocol according to one embodiment of the present disclosure.
Figure 22B:

FIGS. 22A and 22B depict a wound of a 64-year old female without adverse wound healing conditions (no diabetes, no history of smoking cigarettes, walks several miles most days). The wound was present Jun. 9, 2016 until Aug. 22, 2016 without healing, and developed on the lower pretibial area after a minor injury. The zinc oxide bandage protocol (with no central gauze) was taught to the patient, with instructions to change the dressing daily. FIG. 22B depicts the same wound of FIG. 22A after 7 days of treatment using only the peripheral rim portion of the zinc rim protocol without the central drainage gauze. The wound was reduced in size and displayed crusting.

Example 5—Treatment of Non-Healing Wounds with Zinc Oxide Gauze-Only Protocol

Example 5 provides four exemplary cases of previously non-healing skin wounds treated with the zinc oxide methods described in the present disclosure, without central gauze.

Case 9

Figure 24A:
FIGS. 24A-24B are photographs of a wound present for over 4 months, at day 1 (FIG. 24A) and day 10 (FIG. 24B) after treatment with the zinc-only protocol according to one embodiment of the present disclosure.
Figure 24B:
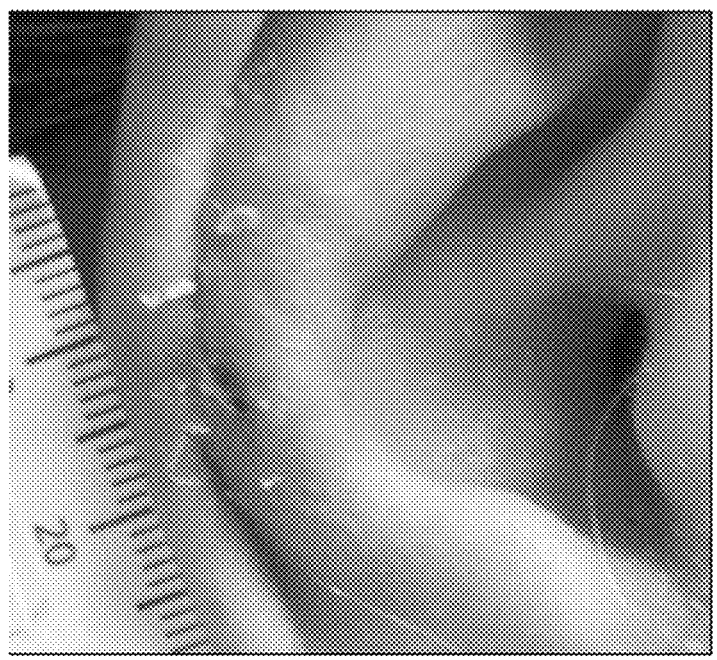

FIG. 24A depicts the right ear of a 67-year-old female with an actinic keratosis on the antihelix of her ear. The wound had previously been treated with liquid nitrogen and topical imiquimod, and four months later the lesion had not healed, but was 12.0 mm$^2$ Zinc dressing was applied according to the zinc-only protocol as described herein, with new dressing applied every two days. After showering, saline soaks for 20 minutes were used before applying the zinc dressing. The wound had healed to 2.8 mm$^2$ after 10 days (FIG. 24B), sufficient healing such that it was subsequently left open to the air.

Case 10

Figure 25A:
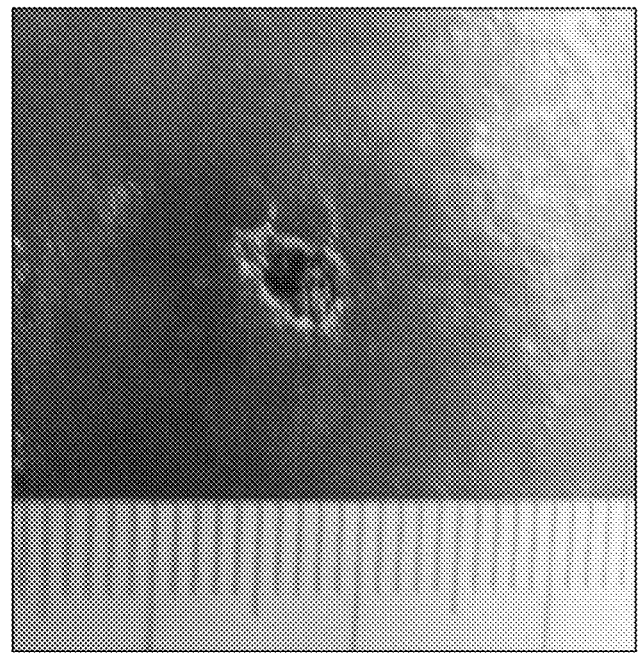
FIGS. 25A-25B are photographs of a wound at day 1 (FIG. 25A) and day 8 (FIG. 25B) after treatment with the zinc-only protocol according to one embodiment of the present disclosure.
Figure 25B:
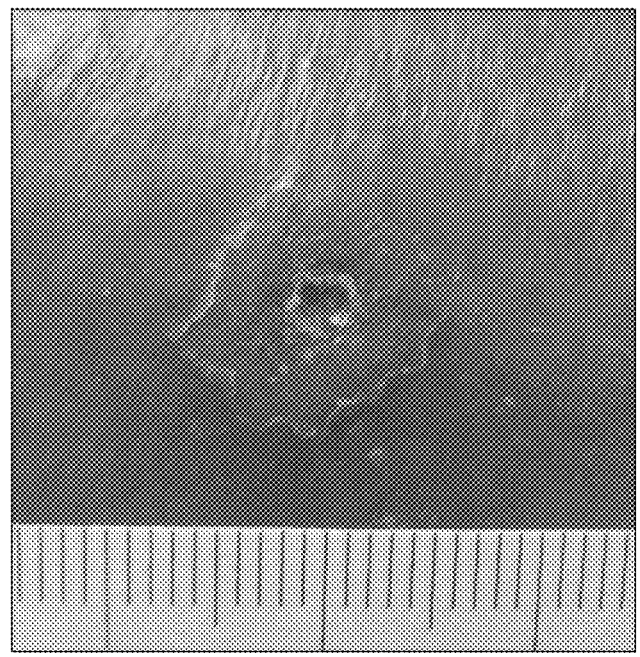

FIG. 25A depicts a non-healing wound of a 76-year-old male, the 9.7 mm$^2$ wound resulting from an injury from an exposed nail on the pretibial area seven weeks previously. He had been treated with two courses of oral antibiotics without change noted. There were no predisposing factors for peripheral vascular disease or stasis dermatitis. Examination showed no swelling in the area or in the ankles; the wound was the only abnormality seen. The wound was treated with daily zinc gauze dressings without saline gauze or saline soaks. He was seen in the clinic one week later, with the wound nearly healed (FIG. 25B).

Case 11

Figure 26A:
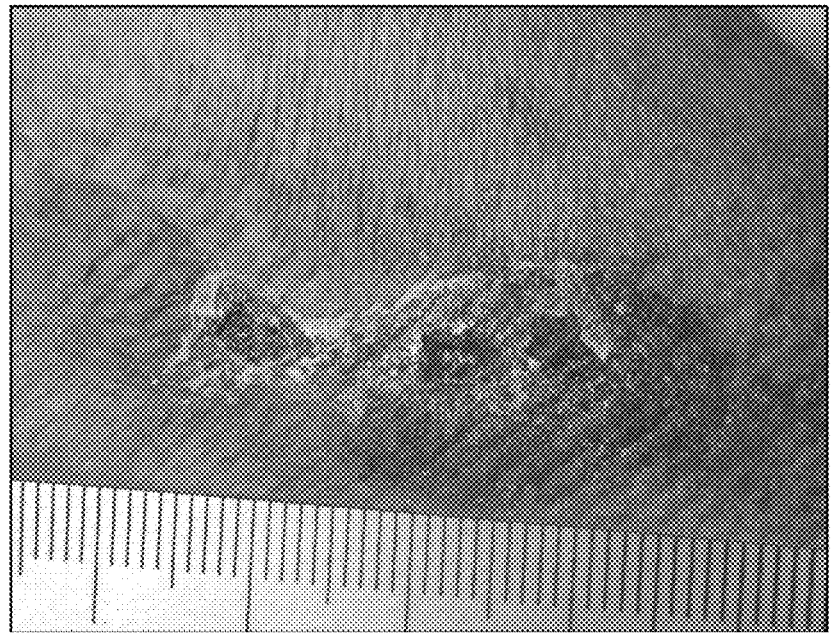
FIGS. 26A-26B are photographs of a wound at day 1 (FIG. 26A) and day 13 (FIG. 26B) after treatment with the zinc-only protocol according to one embodiment of the present disclosure.
Figure 26B:

FIG. 26A depicts a non-healing wound of an 89-year-old male with recurrent stasis dermatitis, with a wound area of 15.6 mm$^2$. The venous stasis ulcer on the leg had previously been treated with zinc gauze and central saline gauze. When the lesion was nearly healed (FIG. 26A), zinc gauze alone was used. On day 13, the lesion was healed (FIG. 26B). The lesion had not recurred on follow-up visit, 16 months later.

Case 12

Figure 27A:
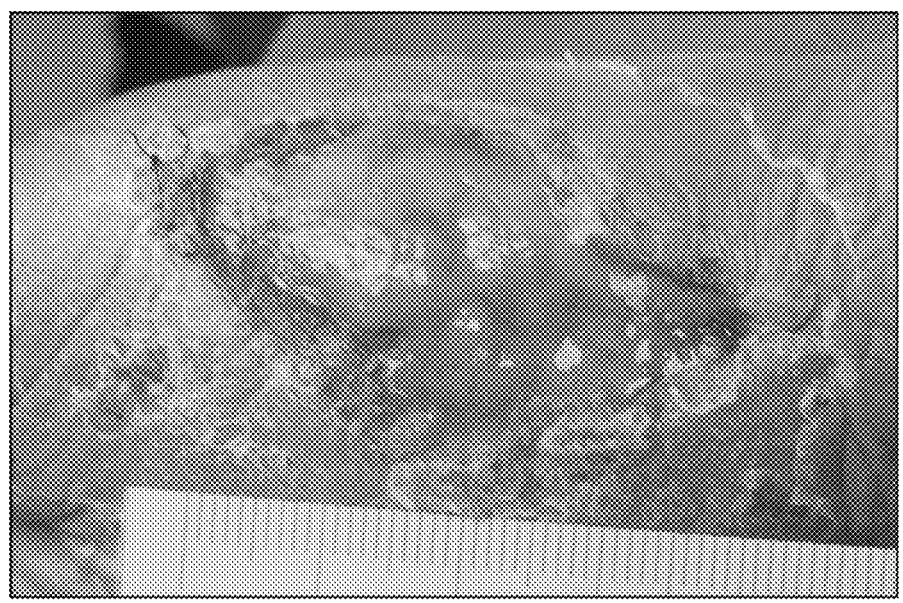
FIGS. 27A-27B are photographs of a wound at day 1 (FIG. 27A) and day 28 (FIG. 27B) after treatment with the zinc-only protocol according to one embodiment of the present disclosure.
Figure 27B:
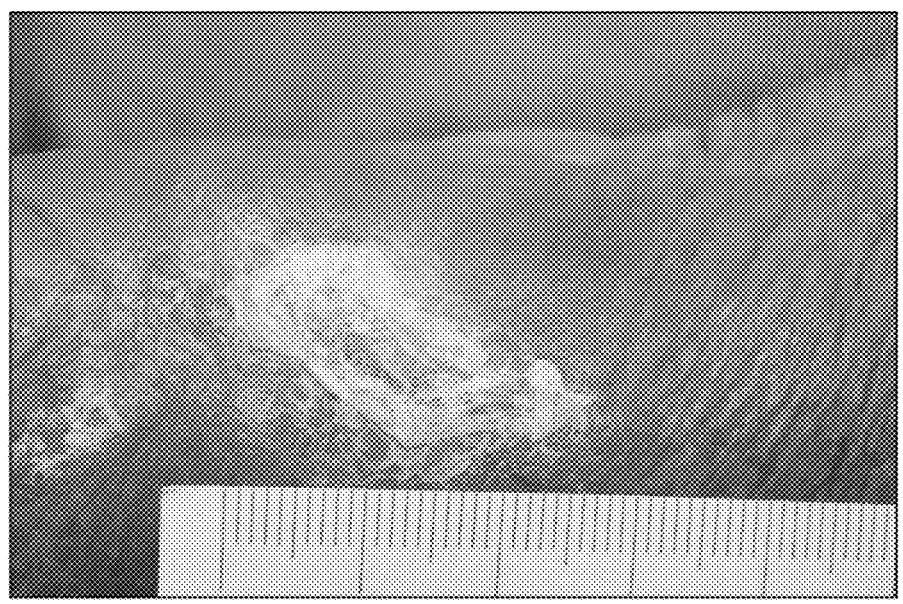

FIG. 27A depicts a non-healing wound of a 92-year-old male, a 555 mm$^2$ well-differentiated squamous cell carcinoma on the left hand. This had been excised and repaired with two-layer closure. At the two-week visit for suture removal, the wound was found to be dehisced (FIG. 27A). He was instructed to change the zinc gauze daily, using 20 minute saline soaks first, per the protocol detailed herein. Central gauze was not use. On day 28, the wound was healed (FIG. 27B).

Results and Discussion of Cases 9-12

Four non-healing wounds were healed or nearly healed with a short period of zinc gauze treatment. Ulcer sizes, duration, and wound healing rates for cases 9-12 are presented in Table 3.

mild tissue debridement was needed. Twenty-minute normal saline soaks were otherwise used before each new zinc dressing was applied.

All patients or their caregivers were able to implement the dressing changes successfully.

Undressed wounds were photographed at dressing changes; a scale was included in each photograph. The wound area was calculated by the best-fit ellipse method, including only the area of the wound lacking epidermis.

All of the compositions and methods disclosed and claimed herein can be made and executed without undue experimentation in light of the present disclosure. While the compositions and methods have been described in terms of particular embodiments, it is apparent to those of skill in the art that variations maybe applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A wound dressing comprising:
   a central drainage gauze configured to directly contact an approximately central area in a wound such that from about 2 mm to about 10 mm of a peripheral area in the wound is not directly contacted by the central drainage gauze; and
   a zinc gauze configured to contact the exposed peripheral area in the wound not directly contacted by the central drainage gauze.

2. The wound dressing of claim 1, wherein the central drainage gauze comprises a porous gauze.

3. The wound dressing of claim 1, wherein the central drainage gauze comprises a multi-ply gauze.

TABLE 3

Initial and final ulcer sizes, ulcer duration, and weekly healing rates of wounds treated with the zinc-only protocol described herein.

| Case | Patient Age | Wound Location | Past History of Tobacco, Diabetes, Relevant systemic illness Wound History | Cause of Wound | Wound history, Previous Treatment | Wound Size mm$^2$ | Healing Rate mm$^2$/day | Days until wound healed sufficiently that patient could be discharged |
|---|---|---|---|---|---|---|---|---|
| 9 | 67 | Ear | No 4 month non-healing wound | Actinic keratosis treatment | Liquid nitrogen cryotherapy and topical imiquimod 4 months earlier | 12 | 0.92 | 10 |
| 10 | 76 | Pretibial (anterior lower leg) | No 7 weeks non-healing wound | Injury from exposed nail | Systemic amoxicillin and sulfa-developed allergic reaction, ulcer did not heal | 9.7 | 1.22 | 8 |
| 11 | 89 | Pretibial (anterior lower leg) | No Months of non-healing venostasis ulcer | Venostasis ulcer | Unna gauze and saline dressing | 15.6 | 1.20 | 13 |
| 12 | 92 | Left hand | No Sutured squamous cell carcinoma site had dehisced. | Dehiscence of surgical wound | None | 555 | 19.82 | 28 |

Materials and Methods for Cases 9-12

Zinc-Only Protocol

The wounds were covered with 3 layers of Econo-Paste Unna. The zinc gauze was secured with latex-free Flex-Band Fabric Adhesive Bandage, of a size to fit the wound (see FIG. 23A). For large wounds, Telfa non-stick pads are covered with Micropore paper adhesive. Dressings were changed every 1-2 days after showering. Wet-to-dry saline soaks were used after showering if exudate was heavy or 4. The wound dressing of claim 1, wherein the zinc gauze comprises a gauze impregnated with one or more of: zinc oxide, zinc sulfate, zinc pyrithione, and zinc gluconate; or one or more of: zinc oxide, zinc sulfate, zinc pyrithione, and zinc gluconate is present on a surface of the gauze.

5. A wound dressing kit comprising:
 a large wound dressing or dressing assembly, or both a small or low exudate wound dressing or dressing assembly and a large wound dressing or dressing assembly, the small or low exudate wound dressing or dressing assembly comprising:
  a zinc gauze configured to occupy an entirety of an exposed wound; and
  a retention layer configured to retain the zinc gauze on the exposed wound; and
 the large wound dressing or dressing assembly comprises:
  a central drainage gauze configured to directly contact an approximately central area in a wound such that from about 2 mm to about 10 mm of a peripheral area in the wound is not directly contacted by the central drainage gauze; and
  a zinc gauze configured to contact the exposed peripheral area in the wound not directly contacted by the central drainage gauze.

6. The wound dressing kit according to claim 5, further comprising a physiological saline solution.

7. The wound dressing kit according to claim 5, wherein the large wound dressing or dressing assembly further comprises a retention layer.

8. The wound dressing kit according to claim 5, wherein the zinc gauze is affixed to an adhesive strip.

9. The wound dressing kit of claim 5, wherein the central drainage gauze comprises a porous gauze.

10. The wound dressing kit of claim 5, wherein the central drainage gauze comprises a multi-ply gauze.

11. The wound dressing kit of claim 5, wherein the zinc gauze comprises a gauze impregnated with one or more of: zinc oxide, zinc sulfate, zinc pyrithione, and zinc gluconate; or one or more of: zinc oxide, zinc sulfate, zinc pyrithione, and zinc gluconate is present on a surface of the gauze.

12. A method to dress a wound, the method comprising:
 providing a wound dressing kit according to claim 5;
 placing the central drainage gauze approximately centrally in the wound, wherein the central drainage gauze leaves an exposed periphery in the wound having a width of about 2 mm to about 10 mm;
 placing the zinc gauze over the wound and contacting the zinc gauze with the exposed periphery in the wound; and
 securing the dressing in place.

13. The method to dress a wound according to claim 12, further comprising saturating the central drainage gauze with a physiological solution.

14. The method to dress a wound according to claim 13, wherein the central drainage gauze is saturated either before or after being placed approximately centrally in the wound.

15. The method of claim 6, wherein the central drainage gauze comprises a porous gauze.

16. The method of claim 6, wherein the central drainage gauze comprises a multi-ply gauze.

17. The method of claim 6, wherein the zinc gauze comprises a gauze impregnated with one or more of: zinc oxide, zinc sulfate, zinc pyrithione, and zinc gluconate; or one or more of: zinc oxide, zinc sulfate, zinc pyrithione, and zinc gluconate is present on a surface of the gauze.

* * * * *